United States Patent
Morton et al.

(10) Patent No.: US 10,007,019 B2
(45) Date of Patent: *Jun. 26, 2018

(54) COMPACT MOBILE CARGO SCANNING SYSTEM

(71) Applicant: Rapiscan Systems, Inc., Torrance, CA (US)

(72) Inventors: Edward James Morton, Guildford (GB); Francis Baldwin, Petersfield (GB); Andreas F. Kotowski, Rancho Palos Verdes, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/689,268

(22) Filed: Apr. 17, 2015

(65) Prior Publication Data

US 2016/0025889 A1 Jan. 28, 2016

Related U.S. Application Data

(63) Continuation of application No. 14/104,637, filed on Dec. 12, 2013, now Pat. No. 9,052,403, which is a (Continued)

(51) Int. Cl.
*G01N 23/06* (2018.01)
*G01V 5/00* (2006.01)
*H05G 1/02* (2006.01)

(52) U.S. Cl.
CPC .......... *G01V 5/0016* (2013.01); *G01V 5/0066* (2013.01); *H05G 1/02* (2013.01); *G01N 2223/639* (2013.01)

(58) Field of Classification Search
CPC ............. G01N 2223/639; G01N 23/04; G01N 23/046; G01N 2223/419; G01N 23/20;
(Continued)

(56) References Cited

U.S. PATENT DOCUMENTS 2,420,845 A 5/1947 Slack
2,636,619 A 4/1953 Alexander
(Continued)

FOREIGN PATENT DOCUMENTS

DE 2729353 A1 1/1979
DE 3214910 A1 5/1983
(Continued)

OTHER PUBLICATIONS

US 5,987,079, 11/1999, Scott (withdrawn)
(Continued)

*Primary Examiner* — Irakli Kiknadze
(74) *Attorney, Agent, or Firm* — Novel IP

(57) ABSTRACT

The present invention is a self-contained mobile inspection system and method and, more specifically, improved methods and systems for detecting materials concealed within a wide variety of receptacles and/or cargo containers. In particular, the present invention is an improved method and system with a novel boom structure that reduces the weight of the boom. The single, light-weight boom of the inspection system is relatively compact in a stowed configuration and has a low height and center of gravity lending to greater maneuverability.

20 Claims, 18 Drawing Sheets

Related U.S. Application Data continuation of application No. 13/598,945, filed on Aug. 30, 2012, now Pat. No. 8,668,386, which is a continuation of application No. 12/784,630, filed on May 21, 2010, now Pat. No. 8,275,091, which is a continuation-in-part of application No. 12/339,591, filed on Dec. 19, 2008, now Pat. No. 7,963,695, which is a continuation-in-part of application No. 11/948,814, filed on Nov. 30, 2007, now Pat. No. 7,517,149, which is a continuation of application No. 10/915,687, filed on Aug. 9, 2004, now Pat. No. 7,322,745, which is a continuation-in-part of application No. 10/201,543, filed on Jul. 23, 2002, now Pat. No. 6,843,599, said application No. 12/339,591 is a continuation-in-part of application No. 12/051,910, filed on Mar. 20, 2008, now Pat. No. 7,519,148, which is a continuation of application No. 11/622,560, filed on Jan. 12, 2007, now Pat. No. 7,369,643, which is a continuation-in-part of application No. 10/915,687, said application No. 12/784,360 is a continuation-in-part of application No. 12/263,160, filed on Oct. 31, 2008, now Pat. No. 7,783,004, which is a continuation-in-part of application No. 10/915,687, said application No. 12/784,630 is a continuation-in-part of application No. 12/349,534, filed on Jan. 7, 2009, now Pat. No. 7,720,195, which is a continuation of application No. 10/939,986, filed on Sep. 13, 2004, now Pat. No. 7,486,768, which is a continuation-in-part of application No. 10/915,687.

(60) Provisional application No. 61/180,471, filed on May 22, 2009, provisional application No. 60/493,935, filed on Aug. 8, 2003, provisional application No. 61/014,814, filed on Dec. 19, 2007, provisional application No. 60/984,786, filed on Nov. 2, 2007, provisional application No. 60/502,498, filed on Sep. 12, 2003.

(58) Field of Classification Search
CPC ......... G01N 23/203; G01N 2223/1016; G01N 2223/306; G01N 2223/3307; G01N 23/201; G01N 2223/401; G01N 23/20083; G01N 24/084; G01N 2223/076; G01N 2223/423; G01N 2223/612; G01N 23/02; G01N 23/06; G01N 23/18; G01N 2223/204; G01N 2223/628; G01N 2223/631; G01N 23/00; G01N 23/083; G01V 5/0016; G01V 5/0066; H05G 1/02; A61B 6/4441; A61B 6/032; A61B 6/4464; A61B 6/027; A61B 6/4085; A61B 6/4405; A61B 6/4458; A61B 6/502; A61B 6/04; A61B 6/466; A61B 6/025; A61B 6/4429; A61B 6/4452; A61B 6/583; A61B 6/0457; A61B 6/06; A61B 6/482; A61B 6/05
USPC ............................ 378/57, 86, 196, 198, 102
See application file for complete search history.

(56) References Cited

U.S. PATENT DOCUMENTS

| | | | |
|---|---|---|---|
| 2,831,123 A | 4/1958 | Daly | |
| 2,885,069 A | 5/1959 | Bowen | |
| 2,952,790 A | 9/1960 | Steen | |
| 2,971,433 A | 2/1961 | Akin | |
| 3,032,207 A * | 5/1962 | McIntyre | B66C 23/54 212/238 |
| 3,056,510 A * | 10/1962 | Garnett | B66C 23/36 182/2.11 |
| 3,070,399 A | 12/1962 | Bartlett | |
| 3,073,960 A | 1/1963 | Guentner | |
| 3,146,349 A | 8/1964 | Jordan | |
| 3,239,706 A | 3/1966 | Farrell | |
| 3,275,831 A | 9/1966 | Martin | |
| 3,374,355 A | 3/1968 | Parratt | |
| 3,458,026 A | 7/1969 | Lauzon | |
| 3,485,339 A | 12/1969 | Miller | |
| 3,676,783 A | 7/1972 | Kinbara | |
| 3,766,387 A | 10/1973 | Heffan | |
| 3,767,850 A | 10/1973 | Mc | |
| 3,768,645 A | 10/1973 | Conway | |
| 3,770,955 A | 11/1973 | Tomita | |
| 3,784,837 A | 1/1974 | Holmstrom | |
| 3,837,502 A | 9/1974 | Hornagold | |
| 3,904,923 A | 9/1975 | Schwartz | |
| 3,919,467 A | 11/1975 | Peugeot | |
| 3,955,678 A | 5/1976 | Moyer | |
| 3,958,377 A * | 5/1976 | Milner, Jr. | B66F 11/044 182/2.8 |
| 3,961,186 A | 6/1976 | Leunbach | |
| 3,980,889 A | 9/1976 | Haas | |
| 4,047,035 A | 9/1977 | Dennhoven | |
| 4,057,725 A | 11/1977 | Wagner | |
| 4,064,440 A | 12/1977 | Roder | |
| 4,105,922 A | 8/1978 | Lambert | |
| 4,139,771 A | 2/1979 | Dennhoven | |
| 4,164,138 A | 8/1979 | Burkhart | |
| 4,210,811 A | 7/1980 | Dennhoven | |
| 4,216,499 A | 8/1980 | Dennhoven | |
| 4,228,353 A | 10/1980 | Johnson | |
| 4,259,721 A | 3/1981 | Kuznia | |
| 4,266,425 A | 5/1981 | Allport | |
| 4,274,005 A | 6/1981 | Yamamura | |
| 4,340,816 A | 7/1982 | Schott | |
| 4,352,021 A | 9/1982 | Boyd | |
| 4,366,382 A | 12/1982 | Kotowski | |
| 4,380,817 A | 4/1983 | Harding | |
| 4,430,568 A | 2/1984 | Yoshida | |
| 4,468,802 A | 8/1984 | Friedel | |
| 4,481,403 A | 11/1984 | Del | |
| 4,501,011 A | 2/1985 | Hauck | |
| 4,525,854 A | 6/1985 | Molbert | |
| 4,563,707 A | 1/1986 | Kishida | |
| 4,566,113 A | 1/1986 | Doenges | |
| 4,599,740 A | 7/1986 | Cable | |
| 4,602,462 A * | 7/1986 | Anderson | B66F 11/044 182/2.9 |
| 4,626,688 A | 12/1986 | Barnes | |
| 4,641,330 A | 2/1987 | Herwig | |
| 4,672,649 A | 6/1987 | Rutt | |
| 4,675,890 A | 6/1987 | Plessis | |
| 4,709,382 A | 11/1987 | Sones | |
| 4,736,401 A | 4/1988 | Donges | |
| 4,752,948 A | 6/1988 | MacMahon | |
| 4,788,704 A | 11/1988 | Donges | |
| 4,799,247 A | 1/1989 | Annis | |
| 4,809,312 A | 2/1989 | Annis | |
| 4,809,857 A | 3/1989 | Steuck | |
| 4,817,123 A | 3/1989 | Sones | |
| 4,825,454 A | 4/1989 | Annis | |
| 4,831,260 A | 5/1989 | DiBianca | |
| RE32,961 E | 6/1989 | Wagner | |
| 4,853,595 A | 8/1989 | Alfano | |
| 4,864,142 A | 9/1989 | Gomberg | |
| 4,866,439 A | 9/1989 | Kraus | |
| 4,866,745 A | 9/1989 | Akai | |
| 4,868,856 A | 9/1989 | Frith | |
| 4,870,670 A | 9/1989 | Geus | |
| 4,872,188 A | 10/1989 | Lauro | |
| 4,879,735 A | 11/1989 | Owens | |
| 4,884,289 A | 11/1989 | Glockmann | |
| 4,887,604 A | 12/1989 | Shefer | |
| 4,979,137 A | 12/1990 | Gerstenfeld | |
| 4,979,202 A | 12/1990 | Siczek | |
| 4,987,584 A | 1/1991 | Doenges | |
| 4,991,189 A | 2/1991 | Boomgaarden | |

(56) References Cited

U.S. PATENT DOCUMENTS

| | | | |
|---|---|---|---|
| 4,991,708 A | 2/1991 | Francioni | |
| 5,006,299 A | 4/1991 | Gozani | |
| 5,014,293 A | 5/1991 | Boyd | |
| 5,016,767 A * | 5/1991 | Thibault | B66F 11/044 182/2.9 |
| 5,022,062 A | 6/1991 | Annis | |
| 5,033,106 A | 7/1991 | Kita | |
| 5,040,199 A | 8/1991 | Stein | |
| 5,065,418 A | 11/1991 | Bermbach | |
| 5,067,145 A | 11/1991 | Siczek | |
| 5,076,993 A | 12/1991 | Sawa | |
| 5,086,300 A | 2/1992 | Ashmore | |
| 5,091,924 A | 2/1992 | Bermbach | |
| 5,092,451 A | 3/1992 | Jones | |
| 5,097,939 A | 3/1992 | Shanklin | |
| 5,098,640 A | 3/1992 | Gozani | |
| 5,114,662 A | 5/1992 | Gozani | |
| 5,144,191 A | 9/1992 | Jones | |
| 5,179,581 A | 1/1993 | Annis | |
| 5,181,234 A | 1/1993 | Smith | |
| 5,182,764 A | 1/1993 | Peschmann | |
| 5,185,778 A | 2/1993 | Magram | |
| 5,202,932 A | 4/1993 | Cambier | |
| 5,221,843 A | 6/1993 | Alvarez | |
| 5,224,144 A | 6/1993 | Annis | |
| 5,237,598 A | 8/1993 | Albert | |
| 5,243,693 A | 9/1993 | Maron | |
| 5,247,556 A | 9/1993 | Eckert | |
| 5,247,561 A | 9/1993 | Kotowski | |
| 5,253,283 A | 10/1993 | Annis | |
| 5,259,014 A | 11/1993 | Brettschneider | |
| 5,260,983 A | 11/1993 | Ono | |
| 5,272,627 A | 12/1993 | Maschhoff | |
| 5,313,511 A | 5/1994 | Annis | |
| 5,319,547 A | 6/1994 | Krug | |
| 5,321,271 A | 6/1994 | Schonberg | |
| 5,341,916 A | 8/1994 | Doane | |
| 5,367,552 A | 11/1994 | Peschmann | |
| 5,379,334 A | 1/1995 | Zimmer | |
| 5,394,454 A | 2/1995 | Harding | |
| 5,410,156 A | 4/1995 | Miller | |
| 5,412,702 A | 5/1995 | Sata | |
| 5,418,372 A | 5/1995 | Schonberg | |
| 5,430,787 A | 7/1995 | Norton | |
| 5,467,377 A | 11/1995 | Dawson | |
| 5,490,196 A | 2/1996 | Rudich | |
| 5,490,218 A | 2/1996 | Krug | |
| 5,493,596 A | 2/1996 | Annis | |
| 5,505,291 A | 4/1996 | Huang | |
| 5,511,104 A | 4/1996 | Mueller | |
| 5,524,133 A | 6/1996 | Neale | |
| 5,548,123 A | 8/1996 | Perez-Mendez | |
| 5,557,108 A | 9/1996 | Tumer | |
| 5,590,057 A | 12/1996 | Fletcher | |
| 5,600,303 A | 2/1997 | Husseiny | |
| 5,600,700 A | 2/1997 | Krug | |
| 5,604,778 A | 2/1997 | Polacin | |
| 5,606,167 A | 2/1997 | Miller | |
| 5,633,907 A | 5/1997 | Gravelle | |
| 5,634,551 A | 6/1997 | Francioni | |
| 5,638,420 A | 6/1997 | Armistead | |
| 5,638,817 A | 6/1997 | Morgan | |
| 5,642,393 A | 6/1997 | Krug | |
| 5,642,394 A | 6/1997 | Rothschild | |
| 5,660,549 A | 8/1997 | Witt | |
| 5,661,377 A | 8/1997 | Mishin | |
| 5,661,774 A | 8/1997 | Gordon | |
| 5,666,393 A | 9/1997 | Annis | |
| 5,687,210 A | 11/1997 | Maitrejean | |
| 5,689,541 A | 11/1997 | Schardt | |
| 5,692,028 A * | 11/1997 | Geus | G01V 5/0008 378/196 |
| 5,692,029 A | 11/1997 | Husseiny | |
| 5,696,806 A | 12/1997 | Grodzins | |
| 5,712,926 A | 1/1998 | Eberhard | |
| 5,738,202 A | 4/1998 | Ydoate | |
| 5,744,919 A | 4/1998 | Mishin | |
| 5,751,837 A | 5/1998 | Watanabe | |
| 5,763,886 A | 6/1998 | Schulte | |
| 5,764,683 A | 6/1998 | Swift | |
| 5,768,334 A | 6/1998 | Maitrejean | |
| 5,787,145 A | 7/1998 | Geus | |
| 5,796,802 A | 8/1998 | Gordon | |
| 5,805,660 A | 9/1998 | Perion | |
| 5,818,897 A | 10/1998 | Gordon | |
| 5,826,666 A * | 10/1998 | Tozawa | E02F 3/437 172/2 |
| 5,838,758 A | 11/1998 | Krug | |
| 5,838,759 A | 11/1998 | Armistead | |
| 5,841,831 A | 11/1998 | Hell | |
| 5,859,891 A | 1/1999 | Hibbard | |
| 5,870,449 A | 2/1999 | Lee | |
| 5,881,122 A | 3/1999 | Crawford | |
| 5,882,206 A | 3/1999 | Gillio | |
| 5,887,047 A | 3/1999 | Bailey | |
| 5,901,198 A | 5/1999 | Crawford | |
| 5,903,623 A | 5/1999 | Swift | |
| 5,905,806 A | 5/1999 | Eberhard | |
| 5,909,477 A | 6/1999 | Crawford | |
| 5,909,478 A | 6/1999 | Polichar | |
| 5,910,973 A | 6/1999 | Grodzins | |
| 5,930,326 A | 7/1999 | Rothschild | |
| 5,940,468 A | 8/1999 | Huang | |
| 5,949,811 A | 9/1999 | Baba | |
| 5,949,842 A | 9/1999 | Schafer | |
| 5,963,211 A | 10/1999 | Oikawa | |
| 5,966,422 A | 10/1999 | Dafni | |
| 5,970,113 A | 10/1999 | Crawford | |
| 5,974,111 A | 10/1999 | Krug | |
| 5,982,843 A | 11/1999 | Bailey | |
| 5,987,097 A | 11/1999 | Salasoo | |
| 6,018,562 A | 1/2000 | Willson | |
| 6,021,174 A | 2/2000 | Campbell | |
| 6,026,143 A | 2/2000 | Simanovsky | |
| 6,026,171 A | 2/2000 | Hiraoglu | |
| 6,031,888 A | 2/2000 | Ivan | |
| 6,031,890 A | 2/2000 | Bermbach | |
| 6,032,808 A | 3/2000 | Henson | |
| 6,035,014 A | 3/2000 | Hiraoglu | |
| 6,037,597 A | 3/2000 | Karavolos | |
| 6,044,353 A | 3/2000 | Pugliese | |
| 6,056,671 A | 5/2000 | Marmer | |
| 6,058,158 A | 5/2000 | Eiler | |
| 6,067,344 A | 5/2000 | Grodzins | |
| 6,067,366 A | 5/2000 | Simanovsky | |
| 6,073,751 A | 6/2000 | Worzischek | |
| 6,075,871 A | 6/2000 | Simanovsky | |
| 6,076,400 A | 6/2000 | Bechwati | |
| 6,078,642 A | 6/2000 | Simanovsky | |
| 6,081,580 A | 6/2000 | Grodzins | |
| 6,088,423 A | 7/2000 | Krug | |
| 6,091,795 A | 7/2000 | Schafer | |
| 6,094,472 A | 7/2000 | Smith | |
| 6,108,396 A | 8/2000 | Bechwati | |
| 6,111,974 A | 8/2000 | Hiraoglu | |
| 6,118,852 A | 9/2000 | Rogers | |
| 6,122,343 A | 9/2000 | Pidcock | |
| 6,128,365 A | 10/2000 | Bechwati | |
| 6,134,299 A | 10/2000 | Artig | |
| 6,137,895 A | 10/2000 | Al-Sheikh | |
| 6,149,592 A | 11/2000 | Yanof | |
| 6,151,381 A | 11/2000 | Grodzins | |
| 6,163,591 A | 12/2000 | Benjamin | |
| 6,181,765 B1 | 1/2001 | Sribar | |
| 6,183,139 B1 | 2/2001 | Solomon | |
| 6,185,272 B1 | 2/2001 | Hiraoglu | |
| 6,188,745 B1 | 2/2001 | Gordon | |
| 6,188,747 B1 | 2/2001 | Geus | |
| 6,192,101 B1 | 2/2001 | Grodzins | |
| 6,192,104 B1 | 2/2001 | Adams | |
| 6,195,413 B1 | 2/2001 | Geus | |
| 6,195,444 B1 | 2/2001 | Simanovsky | |
| 6,198,795 B1 | 3/2001 | Naumann | |

(56) References Cited

U.S. PATENT DOCUMENTS

| | | | |
|---|---|---|---|
| 6,200,024 B1 * | 3/2001 | Negrelli | A61B 6/4233 378/196 |
| 6,212,251 B1 | 4/2001 | Tomura | |
| 6,216,540 B1 | 4/2001 | Nelson | |
| 6,218,943 B1 | 4/2001 | Ellenbogen | |
| 6,236,709 B1 | 5/2001 | Perry | |
| 6,236,712 B1 | 5/2001 | Tomasetti | |
| 6,246,320 B1 | 6/2001 | Monroe | |
| 6,249,567 B1 | 6/2001 | Rothschild | |
| 6,252,929 B1 | 6/2001 | Swift | |
| 6,256,369 B1 | 7/2001 | Lai | |
| 6,256,404 B1 | 7/2001 | Gordon | |
| 6,269,142 B1 | 7/2001 | Smith | |
| 6,272,230 B1 | 8/2001 | Hiraoglu | |
| 6,278,115 B1 | 8/2001 | Annis | |
| 6,282,260 B1 | 8/2001 | Grodzins | |
| 6,292,533 B1 | 9/2001 | Swift | |
| 6,301,326 B2 | 10/2001 | Bjorkholm | |
| 6,301,327 B1 | 10/2001 | Martens | |
| 6,304,629 B1 | 10/2001 | Conway | |
| 6,317,509 B1 | 11/2001 | Simanovsky | |
| 6,320,933 B1 | 11/2001 | Grodzins | |
| 6,324,249 B1 | 11/2001 | Fazzio | |
| 6,345,113 B1 | 2/2002 | Crawford | |
| 6,347,132 B1 | 2/2002 | Annis | |
| 6,356,620 B1 | 3/2002 | Rothschild | |
| 6,396,899 B2 | 5/2002 | Kuwabara | |
| 6,418,189 B1 | 7/2002 | Schafer | |
| 6,418,194 B1 | 7/2002 | McPherson | |
| 6,421,420 B1 | 7/2002 | Grodzins | |
| 6,424,695 B1 | 7/2002 | Grodzins | |
| 6,427,891 B1 | 8/2002 | Anderson | |
| 6,429,578 B1 | 8/2002 | Danielsson | |
| 6,430,255 B2 | 8/2002 | Fenkart | |
| 6,431,344 B1 | 8/2002 | Emmermann | |
| 6,434,219 B1 | 8/2002 | Rothschild | |
| 6,435,715 B1 | 8/2002 | Betz | |
| 6,438,201 B1 | 8/2002 | Mazess | |
| 6,442,233 B1 | 8/2002 | Grodzins | |
| 6,445,765 B1 | 9/2002 | Frank | |
| 6,446,782 B1 | 9/2002 | Patrick | |
| 6,448,564 B1 | 9/2002 | Johnson | |
| 6,453,003 B1 | 9/2002 | Springer | |
| 6,453,007 B2 | 9/2002 | Adams | |
| 6,456,684 B1 | 9/2002 | Mun | |
| 6,459,755 B1 | 10/2002 | Li | |
| 6,459,761 B1 | 10/2002 | Grodzins | |
| 6,459,764 B1 | 10/2002 | Chalmers | |
| 6,473,487 B1 | 10/2002 | Le | |
| RE37,899 E | 11/2002 | Grodzins | |
| 6,483,894 B2 | 11/2002 | Hartick | |
| 6,507,025 B1 | 1/2003 | Verbinski | |
| 6,528,787 B2 | 3/2003 | Katagami | |
| 6,532,276 B1 | 3/2003 | Hartick | |
| 6,542,574 B2 | 4/2003 | Grodzins | |
| 6,542,578 B2 | 4/2003 | Ries | |
| 6,542,580 B1 | 4/2003 | Carver | |
| 6,543,599 B2 | 4/2003 | Jasinetzky | |
| 6,546,072 B1 | 4/2003 | Chalmers | |
| 6,552,346 B2 | 4/2003 | Verbinski | |
| 6,556,653 B2 | 4/2003 | Hussein | |
| 6,563,903 B2 | 5/2003 | Kang | |
| 6,563,906 B2 | 5/2003 | Hussein | |
| 6,567,496 B1 | 5/2003 | Sychev | |
| 6,580,778 B2 | 6/2003 | Meder | |
| 6,584,170 B2 | 6/2003 | Aust | |
| 6,590,956 B2 | 7/2003 | Fenkart | |
| 6,591,130 B2 | 7/2003 | Shahidi | |
| 6,597,760 B2 | 7/2003 | Beneke | |
| 6,606,516 B2 | 8/2003 | Levine | |
| 6,618,466 B1 | 9/2003 | Ning | |
| 6,621,888 B2 | 9/2003 | Grodzins | |
| 6,629,593 B2 | 10/2003 | Zeitler | |
| 6,636,581 B2 | 10/2003 | Sorenson | |
| 6,636,623 B2 | 10/2003 | Nelson | |
| 6,647,091 B2 | 11/2003 | Fenkart | |
| 6,647,094 B2 | 11/2003 | Harding | |
| 6,647,095 B2 | 11/2003 | Hsieh | |
| 6,653,588 B1 | 11/2003 | Gillard-Hickman | |
| 6,658,087 B2 | 12/2003 | Chalmers | |
| 6,661,876 B2 | 12/2003 | Turner | |
| 6,663,280 B2 | 12/2003 | Doenges | |
| 6,665,373 B1 | 12/2003 | Kotowski | |
| 6,665,433 B2 | 12/2003 | Roder | |
| 6,687,333 B2 | 2/2004 | Carroll | |
| 6,690,766 B2 | 2/2004 | Kresse | |
| 6,707,879 B2 | 3/2004 | McClelland | |
| 6,713,773 B1 | 3/2004 | Lyons | |
| 6,715,533 B2 | 4/2004 | Kresse | |
| 6,721,387 B1 | 4/2004 | Naidu | |
| 6,721,391 B2 | 4/2004 | McClelland | |
| 6,727,506 B2 | 4/2004 | Mallette | |
| 6,735,271 B1 | 5/2004 | Rand | |
| 6,737,652 B2 | 5/2004 | Lanza | |
| 6,744,845 B2 | 6/2004 | Harding | |
| 6,748,043 B1 | 6/2004 | Dobbs | |
| 6,754,298 B2 | 6/2004 | Fessler | |
| 6,760,407 B2 | 7/2004 | Price | |
| 6,763,083 B2 | 7/2004 | Fernandez | |
| 6,763,635 B1 * | 7/2004 | Lowman | B60P 1/5433 378/198 |
| 6,770,884 B2 | 8/2004 | Bryman | |
| 6,775,348 B2 | 8/2004 | Hoffman | |
| 6,785,357 B2 | 8/2004 | Bernardi | |
| 6,788,761 B2 | 9/2004 | Bijjani | |
| 6,812,426 B1 | 11/2004 | Kotowski | |
| 6,813,374 B1 | 11/2004 | Karimi | |
| 6,816,571 B2 | 11/2004 | Bijjani | |
| 6,827,265 B2 | 12/2004 | Knowles | |
| 6,829,585 B1 | 12/2004 | Grewal | |
| 6,830,185 B2 | 12/2004 | Tsikos | |
| 6,837,422 B1 | 1/2005 | Meder | |
| 6,837,432 B2 | 1/2005 | Tsikos | |
| 6,839,134 B2 | 1/2005 | Saito | |
| 6,839,403 B1 | 1/2005 | Kotowski | |
| 6,843,599 B2 | 1/2005 | Le | |
| 6,856,344 B2 | 2/2005 | Frantz | |
| 6,856,667 B2 | 2/2005 | Ellenbogen | |
| 6,859,514 B2 | 2/2005 | Hoffman | |
| 6,869,217 B2 | 3/2005 | Rasche | |
| 6,876,719 B2 | 4/2005 | Ozaki | |
| 6,876,724 B2 | 4/2005 | Zhou | |
| 6,879,657 B2 | 4/2005 | Hoffman | |
| 6,899,540 B1 | 5/2005 | Neiderman | |
| 6,901,135 B2 | 5/2005 | Fox | |
| 6,901,346 B2 | 5/2005 | Tracy | |
| 6,906,329 B2 | 6/2005 | Bryman | |
| 6,907,101 B2 | 6/2005 | Hoffman | |
| 6,920,197 B2 | 7/2005 | Kang | |
| 6,922,455 B2 | 7/2005 | Jurczyk | |
| 6,922,460 B2 | 7/2005 | Skatter | |
| 6,922,461 B2 | 7/2005 | Kang | |
| 6,928,141 B2 | 8/2005 | Carver | |
| 6,933,504 B2 | 8/2005 | Hoffman | |
| 6,934,354 B2 | 8/2005 | Hoffman | |
| 6,937,692 B2 | 8/2005 | Johnson | |
| 6,940,071 B2 | 9/2005 | Ramsden | |
| 6,944,264 B2 | 9/2005 | Bijjani | |
| 6,947,517 B2 | 9/2005 | Hoffman | |
| 6,950,492 B2 | 9/2005 | Besson | |
| 6,950,493 B2 | 9/2005 | Besson | |
| 6,952,163 B2 | 10/2005 | Huey | |
| 6,953,935 B1 | 10/2005 | Hoffman | |
| 6,957,913 B2 | 10/2005 | Renkart | |
| 6,962,289 B2 | 11/2005 | Vatan | |
| 6,965,314 B2 | 11/2005 | Jerry | |
| 6,968,030 B2 | 11/2005 | Hoffman | |
| 6,968,034 B2 | 11/2005 | Ellenbogen | |
| 6,971,577 B2 | 12/2005 | Tsikos | |
| 6,973,158 B2 | 12/2005 | Besson | |
| 6,975,698 B2 | 12/2005 | Katcha | |
| 6,978,936 B2 | 12/2005 | Tsikos | |
| 6,980,627 B2 | 12/2005 | Qiu | |
| 6,990,171 B2 | 1/2006 | Toth | |

(56) References Cited

U.S. PATENT DOCUMENTS

| | | |
|---|---|---|
| 6,990,172 B2 | 1/2006 | Toth |
| 6,991,371 B2 | 1/2006 | Georgeson |
| 6,993,115 B2 | 1/2006 | McGuire |
| 6,996,209 B2 | 2/2006 | Marek |
| 7,010,083 B2 | 3/2006 | Hoffman |
| 7,010,094 B2 | 3/2006 | Grodzins |
| 7,016,459 B2 | 3/2006 | Ellenbogen |
| 7,020,241 B2 | 3/2006 | Beneke |
| 7,020,242 B2 | 3/2006 | Ellenbogen |
| 7,023,956 B2 | 4/2006 | Heaton |
| 7,023,957 B2 | 4/2006 | Bijjani |
| 7,027,553 B2 | 4/2006 | Dunham |
| 7,027,554 B2 | 4/2006 | Gaultier |
| 7,031,430 B2 | 4/2006 | Kaucic |
| 7,031,434 B1 | 4/2006 | Saunders |
| 7,034,313 B2 | 4/2006 | Hoffman |
| 7,039,154 B1 | 5/2006 | Ellenbogen |
| 7,039,159 B2 | 5/2006 | Muenchau |
| 7,042,975 B2 | 5/2006 | Heuscher |
| 7,045,787 B1 | 5/2006 | Verbinski |
| 7,045,788 B2 | 5/2006 | Iwatschenko-Borho |
| 7,046,756 B2 | 5/2006 | Hoffman |
| 7,046,761 B2 | 5/2006 | Ellenbogen |
| 7,046,768 B1 | 5/2006 | Gilevich |
| 7,050,536 B1 | 5/2006 | Fenkart |
| 7,050,541 B2 | 5/2006 | Bittl |
| 7,054,408 B2 | 5/2006 | Jiang |
| 7,062,009 B2 | 6/2006 | Karimi |
| 7,062,011 B1 | 6/2006 | Tybinkowski |
| 7,062,074 B1 | 6/2006 | Beneke |
| 7,064,334 B2 | 6/2006 | Hoffman |
| 7,065,175 B2 | 6/2006 | Green |
| 7,065,179 B2 | 6/2006 | Block |
| 7,068,749 B2 | 6/2006 | Kollegal |
| 7,068,750 B2 | 6/2006 | Toth |
| 7,068,751 B2 | 6/2006 | Toth |
| 7,072,434 B1 | 7/2006 | Tybinkowski |
| 7,076,029 B2 | 7/2006 | Toth |
| 7,078,699 B2 | 7/2006 | Seppi |
| 7,081,628 B2 | 7/2006 | Granfors |
| 7,084,404 B2 | 8/2006 | Hoffman |
| 7,087,902 B2 | 8/2006 | Wang |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,099,434 B2 | 8/2006 | Adams |
| 7,099,435 B2 | 8/2006 | Heumann |
| 7,103,137 B2 | 9/2006 | Seppi |
| 7,110,488 B2 | 9/2006 | Katcha |
| 7,112,797 B2 | 9/2006 | Hoge |
| 7,116,235 B2 | 10/2006 | Alioto |
| 7,116,749 B2 | 10/2006 | Besson |
| 7,116,751 B2 | 10/2006 | Ellenbogen |
| 7,119,553 B2 | 10/2006 | Yang |
| 7,123,681 B2 | 10/2006 | Ellenbogen |
| 7,127,027 B2 | 10/2006 | Hoffman |
| 7,130,374 B1 | 10/2006 | Jacobs |
| RE39,396 E | 11/2006 | Swift |
| 7,133,491 B2 | 11/2006 | Bernardi |
| 7,136,450 B2 | 11/2006 | Ying |
| 7,136,451 B2 | 11/2006 | Naidu |
| 7,139,367 B1 | 11/2006 | Le |
| 7,139,406 B2 | 11/2006 | McClelland |
| 7,142,208 B2 | 11/2006 | Lorenz |
| 7,142,629 B2 | 11/2006 | Edic |
| 7,149,278 B2 | 12/2006 | Arenson |
| 7,149,339 B2 | 12/2006 | Veneruso |
| 7,154,989 B2 | 12/2006 | Ueno |
| 7,155,812 B1 | 1/2007 | Peterson |
| 7,158,611 B2 | 1/2007 | Heismann |
| 7,162,005 B2 | 1/2007 | Bjorkholm |
| 7,162,285 B2 | 1/2007 | Owens |
| 7,164,747 B2 | 1/2007 | Ellenbogen |
| 7,164,750 B2 | 1/2007 | Nabors |
| 7,166,458 B2 | 1/2007 | Ballerstadt |
| 7,166,844 B1 | 1/2007 | Gormley |
| 7,167,539 B1 | 1/2007 | Hoffman |
| 7,173,998 B2 | 2/2007 | Hoffman |
| 7,177,387 B2 | 2/2007 | Yasunaga |
| 7,177,391 B2 | 2/2007 | Chapin |
| 7,187,756 B2 | 3/2007 | Gohno |
| 7,190,757 B2 | 3/2007 | Ying |
| 7,192,031 B2 | 3/2007 | Dunham |
| 7,197,113 B1 | 3/2007 | Katcha |
| 7,197,172 B1 | 3/2007 | Naidu |
| 7,203,276 B2 | 4/2007 | Arsenault |
| 7,203,629 B2 | 4/2007 | Oezis |
| 7,204,125 B2 | 4/2007 | Fine |
| 7,206,379 B2 | 4/2007 | Lemaitre |
| 7,207,713 B2 | 4/2007 | Lowman |
| 7,212,113 B2 | 5/2007 | Zanovitch |
| 7,215,731 B1 | 5/2007 | Basu |
| 7,215,737 B2 | 5/2007 | Li |
| 7,215,738 B2 | 5/2007 | Muenchau |
| 7,218,700 B2 | 5/2007 | Huber |
| 7,218,704 B1 | 5/2007 | Adams |
| 7,224,763 B2 | 5/2007 | Naidu |
| 7,224,765 B2 | 5/2007 | Ellenbogen |
| 7,224,766 B2 | 5/2007 | Jiang |
| 7,224,769 B2 | 5/2007 | Turner |
| 7,233,640 B2 | 6/2007 | Ikhlef |
| 7,236,564 B2 | 6/2007 | Hopkins |
| 7,238,945 B2 | 7/2007 | Hoffman |
| 7,238,951 B2 | 7/2007 | Disdier |
| 7,244,947 B2 | 7/2007 | Polichar |
| 7,247,856 B2 | 7/2007 | Hoge |
| 7,250,940 B2 | 7/2007 | Jayanetti |
| 7,251,310 B2 | 7/2007 | Smith |
| 7,257,189 B2 | 8/2007 | Modica |
| 7,260,170 B2 | 8/2007 | Arenson |
| 7,260,171 B1 | 8/2007 | Arenson |
| 7,260,172 B2 | 8/2007 | Arenson |
| 7,260,173 B2 | 8/2007 | Wakayama |
| 7,260,174 B2 | 8/2007 | Hoffman |
| 7,260,182 B2 | 8/2007 | Toth |
| 7,260,255 B2 | 8/2007 | Polichar |
| 7,263,160 B2 | 8/2007 | Schlomka |
| 7,266,180 B1 | 9/2007 | Saunders |
| 7,272,208 B2 | 9/2007 | Yatsenko |
| 7,272,429 B2 | 9/2007 | Walker |
| 7,274,767 B2 | 9/2007 | Clayton |
| 7,277,577 B2 | 10/2007 | Ying |
| 7,279,120 B2 | 10/2007 | Cheng |
| 7,280,631 B2 | 10/2007 | De |
| 7,282,727 B2 | 10/2007 | Retsky |
| 7,283,604 B2 | 10/2007 | De |
| 7,283,609 B2 | 10/2007 | Possin |
| 7,295,019 B2 | 11/2007 | Yang |
| 7,295,651 B2 | 11/2007 | Delgado |
| 7,298,812 B2 | 11/2007 | Tkaczyk |
| 7,302,083 B2 | 11/2007 | Larson |
| 7,308,073 B2 | 12/2007 | Tkaczyk |
| 7,308,074 B2 | 12/2007 | Jiang |
| 7,308,077 B2 | 12/2007 | Bijjani |
| 7,317,195 B2 | 1/2008 | Eikman |
| 7,317,259 B2 | 1/2008 | Yamauchi |
| 7,317,390 B2 | 1/2008 | Huey |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying |
| 7,330,527 B2 | 2/2008 | Hoffman |
| 7,330,535 B2 | 2/2008 | Arenson |
| 7,333,587 B2 | 2/2008 | De |
| 7,333,588 B2 | 2/2008 | Mistretta |
| 7,333,589 B2 | 2/2008 | Ellenbogen |
| 7,335,887 B1 | 2/2008 | Verbinski |
| 7,336,769 B2 | 2/2008 | Arenson |
| 7,349,525 B2 | 3/2008 | Morton |
| 7,352,843 B2 | 4/2008 | Hu |
| 7,356,174 B2 | 4/2008 | Leue |
| 7,369,463 B1 | 5/2008 | Van Dullemen |
| 7,369,640 B2 | 5/2008 | Seppi |

(56) References Cited

U.S. PATENT DOCUMENTS

| | | | |
|---|---|---|---|
| 7,369,643 B2 | 5/2008 | Kotowski |
| 7,372,040 B2 | 5/2008 | Polichar |
| 7,372,944 B2 | 5/2008 | Bernhardt |
| 7,379,530 B2 | 5/2008 | Hoff |
| 7,386,092 B2 | 6/2008 | Kang |
| 7,397,891 B2 | 7/2008 | Johnson |
| 7,400,701 B1 | 7/2008 | Cason |
| 7,420,174 B2 | 9/2008 | Kurita |
| 7,429,738 B2 | 9/2008 | Li |
| 7,440,543 B2 | 10/2008 | Morton |
| 7,453,987 B1 | 11/2008 | Richardson |
| 7,460,639 B2 | 12/2008 | Tudor |
| 7,470,914 B2 | 12/2008 | Li |
| 7,475,428 B2 | 1/2009 | Smith |
| 7,475,866 B2 | 1/2009 | Hu |
| 7,483,510 B2 | 1/2009 | Carver |
| 7,483,511 B2 | 1/2009 | Bendahan |
| 7,486,768 B2 | 2/2009 | Allman |
| 7,492,855 B2 | 2/2009 | Hopkins |
| 7,500,931 B2 | 3/2009 | Rosemeier |
| 7,505,556 B2 | 3/2009 | Chalmers |
| 7,505,557 B2 | 3/2009 | Modica |
| 7,505,562 B2 | 3/2009 | Dinca |
| 7,512,215 B2 | 3/2009 | Morton |
| 7,517,149 B2 | 4/2009 | Agrawal |
| 7,519,148 B2 | 4/2009 | Kotowski |
| 7,525,101 B2 | 4/2009 | Grodzins |
| 7,526,064 B2 | 4/2009 | Akery |
| 7,538,325 B2 | 5/2009 | Mishin |
| 7,547,888 B2 | 6/2009 | Cooke |
| 7,551,714 B2 | 6/2009 | Rothschild |
| 7,551,715 B2 | 6/2009 | Rothschild |
| 7,551,718 B2 | 6/2009 | Rothschild |
| 7,555,099 B2 | 6/2009 | Rothschild |
| 7,564,939 B2 | 7/2009 | Morton |
| 7,580,505 B2 | 8/2009 | Kang |
| 7,593,506 B2 | 9/2009 | Cason |
| 7,593,510 B2 | 9/2009 | Rothschild |
| 7,649,976 B2 | 1/2010 | Georgeson |
| 7,663,109 B2 | 2/2010 | Kang |
| 7,684,538 B2 | 3/2010 | Morton |
| 7,720,195 B2 | 5/2010 | Allman |
| 7,724,869 B2 | 5/2010 | Wang |
| 7,734,066 B2 | 6/2010 | Delia |
| 7,738,687 B2 | 6/2010 | Tortora |
| 7,741,612 B2 | 6/2010 | Clothier |
| 7,742,568 B2 | 6/2010 | Smith |
| 7,760,103 B2 | 7/2010 | Frank |
| 7,762,760 B2 | 7/2010 | Takehara |
| 7,769,133 B2 | 8/2010 | Carver |
| 7,783,003 B2 | 8/2010 | Clayton |
| 7,783,004 B2 | 8/2010 | Kotowski |
| 7,796,734 B2 | 9/2010 | Mastronardi |
| 7,800,073 B2 | 9/2010 | Clothier |
| 7,809,104 B2 | 10/2010 | Foland |
| 7,809,109 B2 | 10/2010 | Mastronardi |
| 7,817,775 B2 | 10/2010 | Kang |
| 7,817,776 B2 | 10/2010 | Agrawal |
| 7,835,486 B2 | 11/2010 | Basu |
| 7,860,213 B2 | 12/2010 | Akery |
| 7,876,879 B2 | 1/2011 | Morton |
| 7,876,880 B2 | 1/2011 | Kotowski |
| 7,885,375 B2 | 2/2011 | Bernard |
| 7,903,783 B2 | 3/2011 | Modica |
| 7,952,079 B2 | 5/2011 | Neustadter |
| 7,957,506 B2 | 6/2011 | Smith |
| 7,963,695 B2 * | 6/2011 | Kotowski ............... G01N 23/04 378/198 |
| 7,965,695 B2 | 6/2011 | Valko |
| 7,973,697 B2 | 7/2011 | Reilly |
| 7,991,113 B2 | 8/2011 | Carver |
| 7,991,117 B2 | 8/2011 | Chen |
| 7,995,705 B2 | 8/2011 | Allman |
| 8,000,436 B2 | 8/2011 | Seppi |
| 8,031,903 B2 | 10/2011 | Paresi |
| 8,059,781 B2 | 11/2011 | Agrawal |
| 8,148,693 B2 | 4/2012 | Ryge |
| 8,170,177 B2 | 5/2012 | Akery |
| 8,173,970 B2 | 5/2012 | Inbar |
| 8,194,822 B2 | 6/2012 | Rothschild |
| 8,263,938 B2 | 9/2012 | Bjorkholm |
| 8,275,091 B2 | 9/2012 | Morton |
| 8,350,747 B2 | 1/2013 | Delia |
| 8,356,937 B2 | 1/2013 | Kotowski |
| 8,385,501 B2 | 2/2013 | Allman |
| 8,389,941 B2 | 3/2013 | Bendahan |
| 8,389,942 B2 | 3/2013 | Morton |
| 8,401,147 B2 | 3/2013 | Ryge |
| 8,433,036 B2 | 4/2013 | Morton |
| 8,437,448 B2 | 5/2013 | Langeveld |
| 8,451,974 B2 | 5/2013 | Morton |
| 8,457,275 B2 | 6/2013 | Akery |
| 8,483,356 B2 | 7/2013 | Bendahan |
| 8,491,189 B2 | 7/2013 | Kotowski |
| 8,498,376 B2 | 7/2013 | Modica |
| 8,502,699 B2 | 8/2013 | Zerwekh |
| 8,503,605 B2 | 8/2013 | Morton |
| 8,579,506 B2 | 11/2013 | Morton |
| 8,582,720 B2 | 11/2013 | Morton |
| 8,644,453 B2 | 2/2014 | Morton |
| 8,668,386 B2 * | 3/2014 | Morton ............... G01V 5/0016 378/198 |
| 8,687,765 B2 | 4/2014 | Kotowski |
| 8,735,833 B2 | 5/2014 | Morto |
| 8,744,033 B2 | 6/2014 | Oosaka |
| 8,798,232 B2 | 8/2014 | Bendahan |
| 8,831,176 B2 | 9/2014 | Morto |
| 8,837,670 B2 | 9/2014 | Akery |
| 2002/0031202 A1 | 3/2002 | Callerame |
| 2002/0038753 A1 | 4/2002 | Ursu |
| 2002/0045152 A1 | 4/2002 | Viscardi |
| 2003/0023592 A1 | 1/2003 | Modica |
| 2003/0085163 A1 | 5/2003 | Chan |
| 2004/0101098 A1 | 5/2004 | Bijjani |
| 2004/0141584 A1 | 7/2004 | Bernardi |
| 2004/0178339 A1 | 9/2004 | Gentile |
| 2004/0213378 A1 | 10/2004 | Zhou |
| 2004/0258305 A1 | 12/2004 | Burnham |
| 2005/0008119 A1 | 1/2005 | McClelland |
| 2005/0023479 A1 | 2/2005 | Grodzins |
| 2005/0031076 A1 | 2/2005 | McClelland |
| 2005/0100135 A1 | 5/2005 | Lowman |
| 2005/0117683 A1 | 6/2005 | Mishin |
| 2005/0117700 A1 | 6/2005 | Peschmann |
| 2005/0226364 A1 | 10/2005 | Bernard |
| 2005/0251397 A1 | 11/2005 | Zanovitch |
| 2006/0056584 A1 | 3/2006 | Allman |
| 2006/0115109 A1 | 6/2006 | Whitson |
| 2006/0140341 A1 | 6/2006 | Carver |
| 2006/0274916 A1 | 12/2006 | Chan |
| 2007/0009088 A1 | 1/2007 | Edic |
| 2007/0085010 A1 | 4/2007 | Letant |
| 2007/0194909 A1 | 8/2007 | Garfield |
| 2007/0217572 A1 | 9/2007 | Kotowski |
| 2008/0056432 A1 | 3/2008 | Pack |
| 2008/0089476 A1 | 4/2008 | Chen |
| 2008/0211431 A1 | 9/2008 | Mishin |
| 2011/0176660 A1 | 7/2011 | Morton |
| 2011/0216881 A1 | 9/2011 | Modica |
| 2012/0177176 A1 | 7/2012 | Carver |
| 2013/0039472 A1 | 2/2013 | Morton |

FOREIGN PATENT DOCUMENTS

| | | |
|---|---|---|
| EP | 77018 | 4/1983 |
| EP | 0077018 A1 | 4/1983 |
| EP | 0176314 | 4/1986 |
| EP | 0261984 A2 | 3/1988 |
| EP | 0287707 | 10/1988 |
| EP | 0417965 | 3/1991 |
| EP | 0432568 | 6/1991 |
| EP | 0531993 A1 | 3/1993 |
| EP | 0584871 A1 | 3/1994 |
| EP | 0864884 A2 | 9/1998 |

(56) References Cited

FOREIGN PATENT DOCUMENTS

| | | |
|---|---|---|
| EP | 0919186 A2 | 6/1999 |
| EP | 0924742 A2 | 6/1999 |
| EP | 0930046 A2 | 7/1999 |
| EP | 0963925 A2 | 12/1999 |
| EP | 0972743 A1 * | 1/2000 ............ B66F 11/046 |
| EP | 1277439 A1 | 1/2003 |
| EP | 1374776 A1 | 1/2004 |
| EP | 1413898 A1 | 4/2004 |
| EP | 2255224 | 12/2010 |
| FR | 2328280 A1 | 5/1977 |
| GB | 1497396 A | 1/1978 |
| GB | 1526041 A | 9/1978 |
| GB | 2015245 A | 9/1979 |
| GB | 2089109 A | 6/1982 |
| GB | 2212903 A | 8/1989 |
| GB | 2255634 A | 11/1992 |
| GB | 2277013 A | 10/1994 |
| GB | 2337032 A | 11/1999 |
| GB | 2404431 | 2/2005 |
| GB | 2409268 A | 6/2005 |
| GB | 2424065 A | 9/2006 |
| GB | 2437777 A | 11/2007 |
| GB | 2438317 A | 11/2007 |
| GB | 2470161 | 11/2010 |
| GB | 2470163 | 11/2010 |
| GB | 2470330 | 11/2010 |
| JP | 570175247 | 10/1982 |
| JP | 59016254 | 1/1984 |
| JP | 5975549 | 4/1984 |
| JP | 600015546 | 1/1985 |
| JP | 600021440 | 2/1985 |
| JP | H10211196 A | 8/1998 |
| JP | H11230918 A | 8/1999 |
| JP | 2001176408 | 6/2001 |
| JP | 2001233440 A | 8/2001 |
| JP | 2003126075 A | 5/2003 |
| JP | 2004000605 A | 1/2004 |
| JP | 2005013768 A | 1/2005 |
| WO | 9528715 A2 | 10/1995 |
| WO | 9802763 A1 | 1/1998 |
| WO | 9803889 A1 | 1/1998 |
| WO | 9820366 A1 | 5/1998 |
| WO | 9855851 A1 | 12/1998 |
| WO | 9939189 A2 | 8/1999 |
| WO | 9960387 A2 | 11/1999 |
| WO | 0033060 A2 | 6/2000 |
| WO | 0159485 A1 | 8/2001 |
| WO | 2001059485 | 8/2001 |
| WO | 03051201 A2 | 6/2003 |
| WO | 03105159 | 12/2003 |
| WO | 2004010127 A1 | 1/2004 |
| WO | 2004037088 | 5/2004 |
| WO | 2004111625 | 12/2004 |
| WO | 2005091227 | 9/2005 |
| WO | 2005098400 A2 | 10/2005 |
| WO | 2006036076 A1 | 4/2006 |
| WO | 2006045019 | 4/2006 |
| WO | 2006078691 A2 | 7/2006 |
| WO | 2006095188 | 9/2006 |
| WO | 2005084351 | 11/2006 |
| WO | 2006135586 | 12/2006 |
| WO | 2007035359 A2 | 3/2007 |
| WO | 2007051092 | 5/2007 |
| WO | 2007055720 A2 | 5/2007 |
| WO | 2007068933 A1 | 6/2007 |
| WO | 2007103216 A2 | 9/2007 |
| WO | 2008017983 A2 | 2/2008 |
| WO | 2009027667 A2 | 3/2009 |
| WO | 2009088706 | 9/2009 |
| WO | 2009106803 | 9/2009 |
| WO | 2009106815 | 9/2009 |
| WO | 2009106857 | 9/2009 |
| WO | 2009137698 | 11/2009 |
| WO | 2009141613 | 11/2009 |
| WO | 2009141615 | 11/2009 |
| WO | 2009150416 A2 | 12/2009 |
| WO | 2010135620 | 1/2011 |
| WO | 2011008718 | 1/2011 |
| WO | 2011069024 A1 | 6/2011 |
| WO | 2011087861 | 7/2011 |
| WO | 2011095810 | 8/2011 |
| WO | 2012109273 | 8/2012 |
| WO | 2012174265 | 12/2012 |

OTHER PUBLICATIONS

Smith C. R. et al: 'Application of 450 kV computed tomography to engine blocks with steel liners' Materials Evaluation vol. 65, No. 5, 2007, pp. 458-461, XP055108238.

International Search Report for PCT/US10/35720, dated Nov. 15, 2010, Rapiscan Security Products, Inc.

International Search Report for PCT/US2008/087654, dated Jul. 6, 2009, Rapiscan Security Products, Inc.

International preliminary report on patentability PCT/US2012/024184, dated Aug. 13, 2013, Rapiscan Systems Inc.

International Search Report PCT/US2012/024184, dated Jul. 27, 2012, Rapiscan Systems Inc.

International Search Report PCT/US2012/042493, dated Oct. 1, 2012, Rapiscan Systems Inc.

International Search Report PCT/GB2009/000515, dated Feb. 23, 2010, Rapiscan Security Products, Inc.

International Search Report for PCT/GB2009/000497, dated Jan. 22, 2010.

International Search Report PCT/GB2009/001444, dated Apr. 6, 2010, Rapiscan Security Products.

International Search Report for PCT/GB2009/000556, dated Feb. 19, 2010, Rapiscan Security Products, Inc.

International Search Report PCT/GB2009/001277, dated Jul. 20, 2010, Rapiscan Systems, Inc.

Mobile X-Ray Inspection Systems, Internet Citation, Feb. 12, 2007, pp. 1-2, URL:http://web.archive.org/web/20070212000928/http://www.bombdetecti- on.com/cat--details.php?catid=20.

Molchanov P A et al: 'Nanosecond gated optical sensors for ocean optic applications' Sensors Applications Symposium, 2006. Proceedings of the 2006 IEEE Houston, Texas,USA Feb. 7-9, 2006, Piscataway, NJ, USA,IEEE, Feb. 7, 2006 (Feb. 7, 2006) , pp. 147-150, XP010917671 ISBN: 978-0-7803-9580-0.

International Search Report for PCT/US10/58809; Rapiscan Systems Inc.; dated Apr. 19, 2011.

International Search Report for PCT/GB2009/001250, dated Mar. 2, 2010, Rapiscan Security Products Inc.

International Search Report for PCT/GB2009/001275, dated Jul. 24, 2009, Rapiscan Security Products Inc.

International Search Report for PCT/US2010/041757, dated Oct. 12, 2010, Rapiscan Systems Inc.

International Bureau of WIPO, International Preliminary Report on Patentability, PCT/US2005/011382, dated Oct. 19, 2006, 7 pages.

Mertz, L.N., et al, "Rotational aperture synthesis for x rays", Journal. Optical Society of America, vol. 3, Dec. 1986, pp. 2167-2170.

International Preliminary Report on Patentability, PCT/US2012/024182, dated Aug. 13, 2013, Rapiscan Systems Inc.

International Search Report, PCT/US2012/024182 dated Aug. 20, 2012, Rapiscan Systems Inc.

International Search Report for PCT/US2010/061908, dated Apr. 2, 2012, Rapiscan Systems, Inc.

International Search Report for PCT/GB2006/000859, dated May 19, 2006, Corus UK Ltd.

International Search Report for PCT/GB2011/050182, dated Dec. 28, 2011.

International Search Report for PCT/US11/21758; dated Jul. 7, 2011, Rapiscan Systems Inc.

International Search Report for PCT/GB2009/000575, dated Apr. 7, 2010, Rapiscan Security Products Inc.

International Search Report for PCT/GB2004/001747, dated Aug. 10, 2004, CXR Ltd.

International Search Report for PCT/US2007/005444, dated Oct. 29, 2007, Telesecurity Sciences, Inc.

(56) References Cited

OTHER PUBLICATIONS

International Search Report for PCT/US2006/11492, dated Oct. 11, 2007, United Technologies Corporation.
Sun Olapiriyakul and Sanchoy Das, Design and analysis of a two-stage security screening and inspection system, Journal of Air Transport Management, vol. 13, Issue 2, Mar. 2007, pp. 67-74.
European Patent Office, International Search Report, International Application No. PCT/US99/28266, dated Sep. 6, 2000, 3 pages.
International Search Report, PCT/US2007/066936; dated Sep. 30, 2008, 5 pages.
International Search Report, PCT/US1998/18642, dated Jul. 7, 1999, 4 pages.
International Search Report, PCT/US1999/028035, dated Sep. 15, 2000, 6 pages.
Written Opinion of the International Searching Authority, PCT/US2007/066936, dated Sep. 30, 2008, 7 pages.
Supplementary European Search Report for EP10778449, completed on Jun. 7, 2017.

* cited by examiner

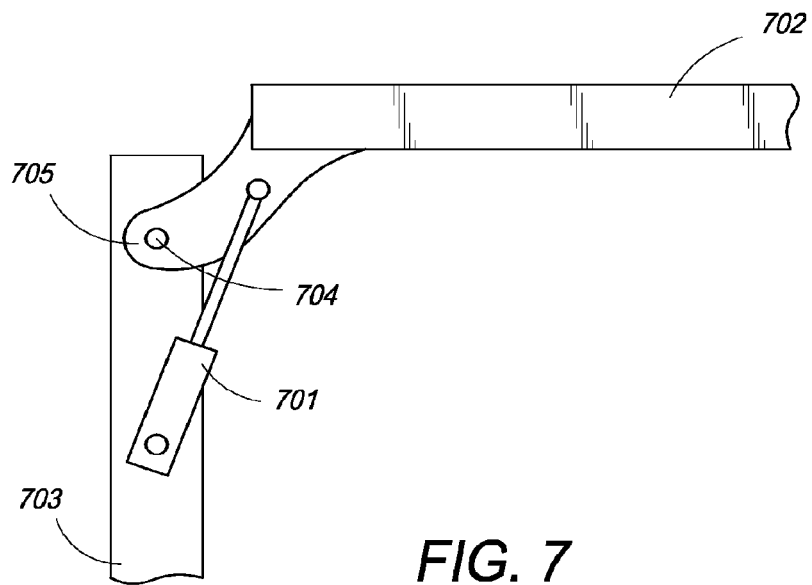
FIG. 7
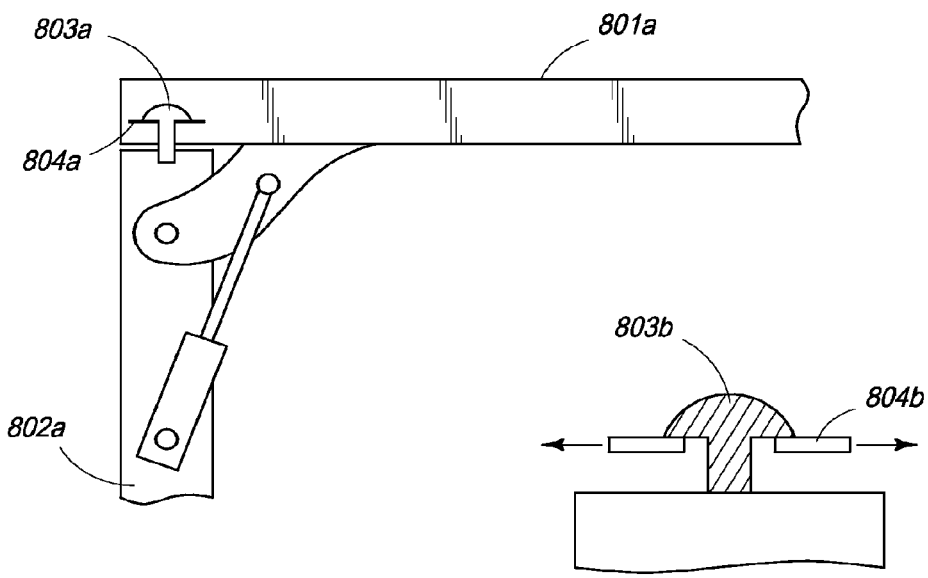
FIG. 8A
FIG. 8B

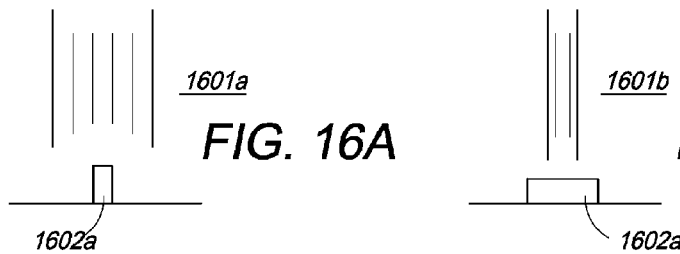
FIG. 16A  FIG. 16B
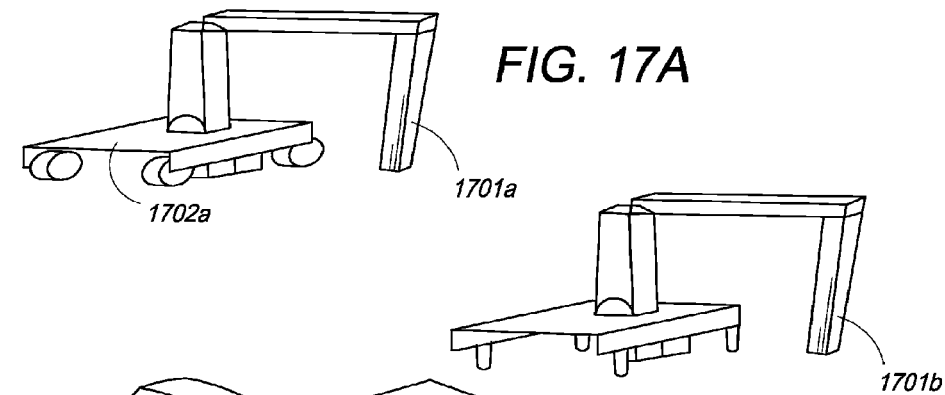
FIG. 17A
FIG. 17B
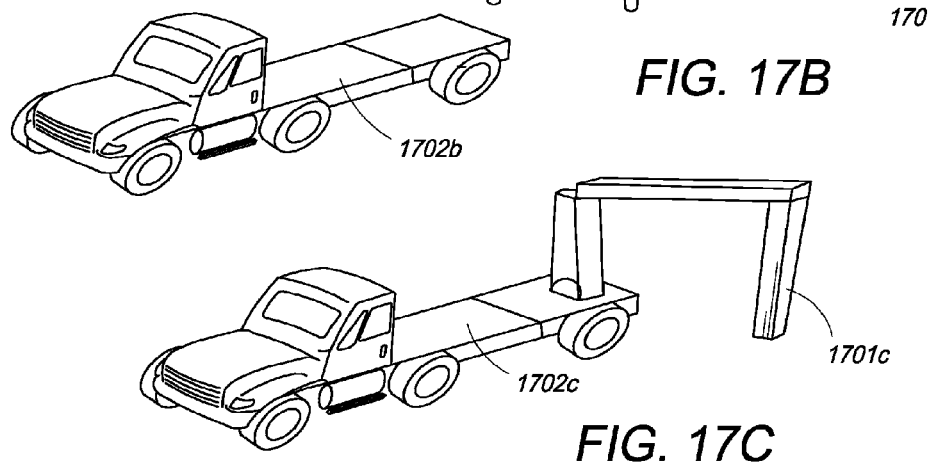
FIG. 17C
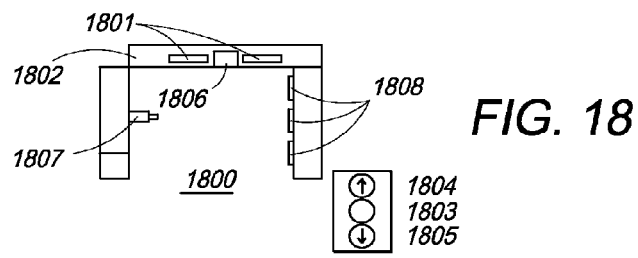
FIG. 18

COMPACT MOBILE CARGO SCANNING SYSTEM

CROSS-REFERENCE

The present application is a continuation of U.S. patent application Ser. No. 12/784,630, filed on May 21, 2010 (the "'630 Application").

The '630 Application relies on U.S. Provisional patent application Ser. No. 61/180,471, filed on May 22, 2009, for priority.

The '630 Application is a continuation-in-part of U.S. patent application Ser. No. 12/339,591, entitled Rotatable Boom Cargo Scanning System, filed on Dec. 19, 2008, which is a continuation-in-part of U.S. patent application Ser. No. 11/948,814, entitled, "Single Boom Cargo Scanning System", filed on Nov. 30, 2007, which is a continuation of U.S. Pat. No. 7,322,745, entitled, "Single Boom Cargo Scanning System", filed on Aug. 9, 2004, which relies on, for priority, U.S. Provisional Patent Application No. 60/493,935, filed on Aug. 8, 2003 and is a continuation-in-part of U.S. patent application Ser. No. 10/201,543, entitled "Self-Contained Portable Inspection System and Method", filed on Jul. 23, 2002 and now U.S. Pat. No. 6,843,599. The '591 application further relies on U.S. Provisional Application No. 61/014,814, filed on Dec. 19, 2007, for priority. The '591 application is also a continuation-in-part of U.S. patent application Ser. No. 12/051,910, entitled "Single Boom Cargo Scanning System", and filed on Mar. 20, 2008, which is a continuation of U.S. Pat. No. 7,369,463, of the same title, filed on Jan. 12, 2007, which is a continuation-in-part of U.S. Pat. No. 7,322,745.

The '630 Application is also a continuation-in-part of U.S. patent application Ser. No. 12/263,160, entitled "Cargo Scanning System", and filed on Oct. 31, 2008, which further relies on U.S. Provisional Patent Application No. 60/984,786, filed on Nov. 2, 2007, for priority, and is a continuation-in-part of U.S. Pat. No. 7,322,745.

The '630 Application is also a continuation-in-part of Ser. No. 12/349,534, which is a continuation of U.S. patent application Ser. No. 10/939,986, entitled "Self-Contained Mobile Inspection System", and filed on Sep. 13, 2004, which is a continuation-in-part of Ser. No. 10/915,687 (issued as U.S. Pat. No. 7,322,745), which is a continuation-in-part of Ser. No. 10/201,543 (issued as U.S. Pat. No. 6,843,599) and further relies on U.S. Provisional Patent Application No. 60/502,498, filed on Sep. 12, 2003, for priority.

All of the above-listed patent applications are herein incorporated by reference.

FIELD

The present application relates generally to a self-contained mobile inspection system and method and, more specifically, to improved methods and systems for detecting materials concealed within a wide variety of receptacles and/or cargo containers. In particular, the present application relates to improved methods and systems for inspecting receptacles and/or cargo containers using a single boom which can be folded, such that the inspection system is light-weight and relatively compact in a stowed configuration and has a low height and center of gravity lending to greater maneuverability.

BACKGROUND

X-ray systems are used for medical, industrial and security inspection purposes because they can cost-effectively generate images of internal spaces not visible to the human eye. Materials exposed to X-ray radiation absorb differing amounts of X-ray radiation and, therefore, attenuate an X-ray beam to varying degrees, resulting in a transmitted level of radiation that is characteristic of the material. The attenuated radiation can be used to generate a useful depiction of the contents of the irradiated object. A typical single energy X-ray configuration used in security inspection equipment may have a fan-shaped or scanning X-ray beam that is transmitted through the object inspected. The absorption of X-rays is measured by detectors after the beam has passed through the object and an image is produced of its contents and presented to an operator.

Trade fraud, smuggling and terrorism have increased the need for such non-intrusive inspection systems in applications ranging from curbside inspection of parked vehicles to scanning in congested or high-traffic ports because transportation systems, which efficiently provide for the movement of commodities across borders, also provide opportunities for the inclusion of contraband items such as weapons, explosives, illicit drugs and precious metals. The term port, while generally accepted as referring to a seaport, also applies to a land border crossing or any port of entry.

With an increase in global commerce, port authorities require additional sea berths and associated container storage space. Additional space requirements are typically met by the introduction of higher container stacks, an expansion of ports along the coastline or by moving inland. However, these scenarios are not typically feasible. Space is generally in substantial demand and short supply. Existing ports operate under a routine that is not easily modified without causing disruption to the entire infrastructure of the port. The introduction of new procedures or technologies often requires a substantial change in existing port operating procedures in order to contribute to the port's throughput, efficiency and operability.

With limited space and a need to expand, finding suitable space to accommodate additional inspection facilities along the normal process route remains difficult. Additionally, selected locations are not necessarily permanent enough for port operators to commit to the long term installation of inspection equipment. Moreover, systems incorporating high-energy X-ray sources, or linear accelerators (LINAC), require either a major investment in shielding material (generally in the form of concrete formations or buildings) or the use of exclusion zones (dead space) around the building itself. In either case, the building footprint is significant depending upon the size of cargo containers to be inspected.

A mobile inspection system offers an appropriate solution to the need for flexible, enhanced inspection capabilities. Because the system is relocatable and investing in a permanent building in which to accommodate the equipment is obviated, site allocation becomes less of an issue and introducing such a system becomes less disruptive. Also, a mobile X-ray system provides operators, via higher throughput, with the ability to inspect a larger array of cargo, shipments, vehicles, and other containers.

Conventional relocatable inspection systems generally comprise at least two booms, wherein one boom will contain a plurality of detectors and the other boom will contain at least one X-ray source. The detectors and X-ray source work in unison to scan the cargo on the moving vehicle. In conventional single boom relocatable inspection systems, the X-ray source is located on a truck or flatbed and the detectors on a boom structure extending outward from the truck. These systems are characterized by moving-scanengine systems wherein the source-detector system moves with respect to a stationary object to be inspected. Also, the detectors and the source of radiation are either mounted on a moveable bed, boom or a vehicle such that they are integrally bound with the vehicle. This limits the flexibility of dismantling the entire system for optimum portability and adjustable deployment to accommodate a wide array of different sized cargo, shipments, vehicles, and other containers. As a result these systems can be complicated to deploy and pose several disadvantages and constraints.

For example, in a moving-scan-engine system the movement of the source and detector, relative to a stationary object, may cause lateral twist and lift and fall of the detector or source, due to movement of the scanner over uneven ground, inducing distortions in the scanned images and faster wear and tear of the scanner system. Systems where the weight of the detector or source is held on a boom require high structural strength for the boom in order to have the boom stable for imaging process, thereby adding more weight into the system. Such systems that require a detector-mounted boom to unfold during deployment may cause an unstable shift of the center of gravity of the system off the base, causing the system to tip over. Further, in the case of moving-scan-engine systems using a "swing arm" boom approach, the driver driving the scanner truck is unable to gauge the possibility of hitting the detector box, mounted on a boom, with a vehicle under inspection (VUI), as the detector box is on the other side of the VUI during scanning and not visible to the driver.

Additionally, with moving-scan-engine systems, the truck supporting the scanner system is always required to move the full weight of the scanner regardless of the size and load of the VUI, putting greater strain on the scanning system. Also disadvantageous in conventional systems is that they suffer from a lack of rigidity, are difficult to implement, and/or have smaller fields of vision.

Accordingly, there is need for improved inspection methods and systems built into a fully self-contained, over-the-road-legal vehicle that can be brought to a site and rapidly deployed for inspection. The improved method and system can, therefore, service multiple inspection sites and set up surprise inspections to thwart contraband traffickers who typically divert smuggling operations from border crossings that have tough interdiction measures to softer crossings with lesser inspection capabilities. Moreover, there is an additional need for methods and systems that require minimal footprint to perform inspection and that use a sufficient range of radiation energy spectrum to encompass safe and effective scanning of light commercial vehicles as well as substantially loaded 20-foot or 40-foot ISO cargo containers. It is important that such scanning is performed without comprising the integrity of the cargo and should ideally be readily deployable in a variety of environments ranging from airports to ports of entry where a single-sided inspection mode needs to be used due to congested environments. Similar needs are addressed in U.S. Pat. No. 6,543,599, entitled "Self-Contained Portable Inspection System and Method", which is herein incorporated by reference in its entirety.

Improved methods and systems are additionally needed to keep the relative position between the radiation source and detector fixed to avoid distortion in images caused by the movement of scanner and/or detectors over uneven ground or due to unstable structures. Moreover, there is a need for improved methods and systems that can provide comprehensive cargo scanning in portable and stationary settings. Specifically, methods and systems are needed in which a single boom is employed for generating quality images for inspection. Further, the system should be mounted on a relocatable vehicle, capable of receiving and deploying the boom.

What is also needed is a single boom cargo scanning system that enables quick and easy deployment, rigidity and tight alignment of the radiation sources and detectors, and a narrow collimated radiation beam, thus allowing for a smaller exclusion zone. In addition, what is needed is an optimal scanning system design that allows for the radiation source to be closer to the Object under Inspection ("OUI"), thereby allowing for higher penetration capability and complete scanning of the target vehicle without corner cutoff. Similar needs are addressed in the U.S. Pat. No. 7,322,745, entitled "Single Boom Cargo Scanning System" which is herein incorporated by reference in its entirety.

Further, in the mobile cargo inspection systems known in the art, the boom structures are typically heavy, thereby causing the overall weight of the scanning system to be close to, or even over the allowable axle load limits. Further, the booms are bulky when stowed such that the vehicle is approximately 4 m high above road level. This makes a mobile scanning system not only difficult to manoeuvre but also restricts its movement in different territories due to the applicable road restrictions on carriage weight. Therefore, there is also a need for a scanning system that can be stowed in a relatively compact area so that it can be easily transported on road, as well as by air. In addition, there is also a need for a scanning system which is light weight, and has a low height and center of gravity in a stowed position, thereby allowing for road transport even in challenging, steep and hilly areas.

What is also needed is a scanning system that can be deployed from a stowed configuration to an operational configuration in operating areas having limited horizontal or vertical clearance.

SUMMARY

The present application is a self-contained mobile inspection system and method for detecting materials concealed within a wide variety of receptacles and/or cargo containers. In particular, the present application is an improved method and system for inspecting receptacles and/or cargo containers using a single boom that can be folded and unfolded, such that the inspection system is relatively compact in a stowed configuration and has a low height lending to greater maneuverability. This, and other embodiments of the present invention, shall be described in greater depth in the drawings and detailed description provided below.

In one embodiment, the present specification discloses an inspection system comprising a vehicle having a first axle proximate to a front of said vehicle and one or more rear axles proximate to a back of said vehicle wherein a first area is bounded by the rear axle extending to the front of said vehicle and a second area is bounded by the rear axle extending to the back of said vehicle; a radiological source; and a boom rotatably attached to said vehicle wherein said boom comprises a first vertical section, a second vertical section and a horizontal section and wherein, when fully deployed, said boom defines an area having a height in a range of 2000 mm to 5300 mm and a width in a range of 2000 mm to 4000 mm, wherein said system weighs less than 20,000 kg and is capable of achieving radiological penetration of at least 30 mm of steel. Optionally, the minimum penetration can be 31 mm, 40 mm, 50 mm, 60 mm, 120 mm or some increment therein.

The radiological source is attached to said vehicle. The radiological source is attached to said vehicle but not attached to said boom. The radiological source is an X-ray source is at least one of a X-ray generator with 100 kVp to 500 kVp tube voltage and 0.1 mA to 20 mA tube current, a 0.8 MV to 2.5 MV linear accelerator source with a dose output rate of less than 0.1 Gy/min at 1 m, and a 2.5 MV to 6 MV linear accelerator source with a output dose rate in a range 0.1 Gy/min at 1 m to 10 Gy/min at 1 m. The vehicle has only one rear axle but may in some configurations have more than one. The boom has a weight and wherein said boom is positioned such that the weight acts substantially over the rear axle. The boom has a weight and wherein said boom is positioned such that the weight acts over the first area.

The boom has a lattice structure comprising a plurality of beam sections connected by a plurality of nodes wherein said structure defines an internal lattice area. The detector or sensor box is connected to an outside the internal lattice area. The detector is positioned within the internal lattice area. The vehicle comprises a plurality of targets wherein each of said targets is on a different part of said vehicle.

The inspection system further comprises a camera in data communication with a controller wherein said camera captures a movement of said targets and wherein said controller determines what portion of said vehicle has moved based on the movement of said target. The controller determines a speed of said vehicle based on said movement of said targets. The controller modulates a frequency at which X-ray data is collected based upon said speed.

In another embodiment, the inspection system comprises a vehicle having a first axle proximate to a front of said vehicle and one or more rear axles proximate to a back of said vehicle wherein a first area is bounded by the rear axle extending to the front of said vehicle and a second area is bounded by the rear axle extending to the back of said vehicle; a radiological source; a boom, having a weight, rotatably attached to said vehicle wherein said boom comprises a first vertical section, a second vertical section and a horizontal section and wherein said weight is positioned to substantially act over said first area and not said second area, wherein said system weighs 15,000 kg or less.

The system is capable of achieving radiological penetration of at least 30 mm of steel. When fully deployed, the boom defines an area having a height in a range of 2000 mm to 5300 mm and a width in a range of 2000 mm to 4000 mm. The radiological source is attached to said vehicle and capable of being moved from a first position to a second position, wherein each of said first and second positions are proximate to said vehicle. The radiological source is an X-ray source is at least one of a X-ray generator with 100 kVp to 500 kVp tube voltage and 0.1 mA to 20 mA tube current, a 0.8 MV to 2.5 MV linear accelerator source with a dose output rate of less than 0.1 Gy/min at 1 m, and a 2.5 MV to 6 MV linear accelerator source with a output dose rate in a range 0.1 Gy/min at 1 m to 10 Gy/min at 1 m. The boom has a lattice structure comprising a plurality of beam sections connected by a plurality of nodes wherein said structure defines an internal lattice area.

BRIEF DESCRIPTION OF THE DRAWINGS

These and other features and advantages of the present invention will be appreciated, as they become better understood by reference to the following detailed description when considered in connection with the accompanying drawings, wherein:

FIG. 7 presents an exemplary mechanism for folding and unfolding the horizontal boom out from the vertical support;

FIG. 8a shows an exemplary locking mechanism which is used when the boom is unfolded;

FIG. 8b shows an exemplary locking mechanism which is used when the boom is unfolded;

FIG. 16a illustrates an alignment of x-ray beam with the detectors;

FIG. 16b illustrates another alignment of x-ray beam with the detectors;

FIG. 17a illustrates an exemplary configuration in which the scanning system of the present invention may be deployed;

FIG. 17b illustrates another exemplary configuration in which the scanning system of the present invention may be deployed;

FIG. 17c illustrates another exemplary configuration in which the scanning system of the present invention may be deployed;

FIG. 18 illustrates an exemplary sensor configuration for control of the X-ray system when operating in drive through mode according to one embodiment of the present invention;

DETAILED DESCRIPTION OF THE INVENTION

The present invention is directed towards a portable inspection system for generating an image representation of target objects using a radiation source, comprising a mobile vehicle; a detector array physically attached to a single, movable boom having a proximal end and a distal end and at least one source of radiation wherein the radiation source is fixedly attached to the proximal end of the boom and adjustable to a desired scanning height. The image is generated by introducing target objects between the radiation source and the detector array, thereby exposing objects to radiation and subsequently detecting the radiation. The boom can be unfolded from a first stowed configuration to a second deployed and operational configuration.

The system of the present invention is advantageous in that it provides a highly compact stowed configuration and has a low height, such that the highest part of the boom does not exceed the height of the drive cab, among other benefits. The inspection system of present invention provides a sturdy deployed configuration with the radiation source and detectors readily aligned and a selectable scan angle position, and can be converted from a stowed configuration to a deployed and operational configuration in areas having limited horizontal and vertical clearance. Further, the inspection system of the present invention is capable of using either a small or a large LINAC, at both high as well as low energies. It may also be used with conventional sources of radiation.

In one embodiment, the present invention is directed toward a new boom configuration for the mobile inspection system, which addresses many of the issues that affect boom designs known in the art. The boom design of the present invention provides for a light weight scanning system, and the boom can also be stowed in a compact manner. This makes the resulting mobile inspection vehicle highly maneuverable. Further, owing to its low axle weights, the mobile inspection vehicle is not subject to any road restrictions and can freely move across all territories in the world.

It should be appreciated that the various mechanical and/or hydraulic movements described herein can occur by manual manipulation of the physical structures or hydraulic components or, as is preferred, by signals transmitted by a controller. In one embodiment, a computing device with a graphical user interface is deployed to receive user commands, transmit user commands to controllers that are in data communication with the various boom, bracket, winch, and/or hydraulic components described herein, and receive data from the controllers indicative of the state of each of the various boom, bracket, winch, and/or hydraulic components described herein. Any computing device and controller system can be used, including laptops, mobile devices, desktop components, and X-ray control centers, and any form of data communication can be used, including wired or wireless communications.

Figure 1:
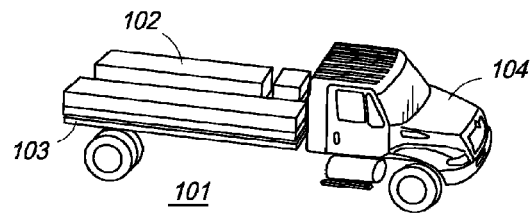
FIG. 1 illustrates the mobile inspection system according to one embodiment of the present invention in transportation mode with the boom stowed on the vehicle.

FIG. 1 illustrates the mobile inspection vehicle 101 of the present invention in its normal transportation mode wherein the boom 102 is stowed on the vehicle. In the embodiment of FIG. 1, the inspection vehicle 101 is a truck and the boom 102 in the stowed condition lies substantially parallel to the bed 103 of the truck 101. The cab 104 of the truck is the highest part of the vehicle, and is typically at an approximate height of 2.6 m from the ground to the highest point. The boom 102 of the present invention is designed such that it is capable of being folded to fit into a space lower than the height of the cab 104, that is, the highest part of the boom 102 does not exceed the height of the drive cab 104.

Persons of ordinary skill in the art should note that the maximum standard overall vehicle dimension of a truck is typically 12 m (L)×2.5 m (W)×4 m (H). However, the overall footprint of the mobile inspection vehicle 101, of the present invention, with the compact boom 102 when stowed thereon is 11 m (L)×2.5 m (W)×4 m (H) in accordance with one embodiment. In an alternate embodiment the footprint of the vehicle 101 is 8 m (L)×2.5 m (W)×2.6 m (H). The compact design of the vehicle 101 with the stowed boom 102, of the present invention, offers a substantially small overall size for the inspection vehicle when used with full size inspection tunnel of 4.6 m (H)×3.5 m (W) typically.

Figure 2A:
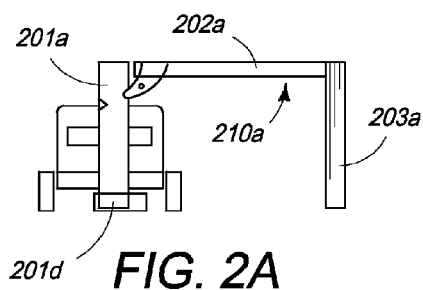
FIG. 2a shows three sections of a boom when fully deployed, according to one embodiment of the present invention.

FIG. 2a shows the boom when fully deployed. The boom comprises three sections: vertical support 201a (connected to an X-ray source 201d), horizontal boom 202a, and vertical boom 203a.

Figure 2B:
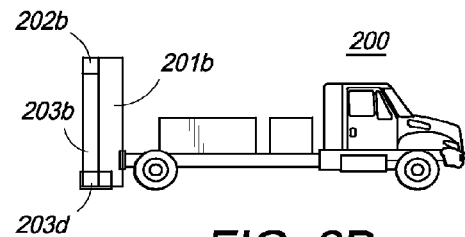
FIG. 2b shows a side view of one embodiment of a mobile inspection vehicle with the boom in a stowed or folded condition.

FIG. 2b shows a side view of the mobile inspection vehicle 200 when it is in use, so that the boom is in deployed condition. As mentioned, the boom design of the present invention comprises three components—vertical support 201b (connected to a X-ray source 203d), horizontal boom 202b and vertical boom 203b, which in the stowed condition can be folded parallel to each other in a manner that the total space occupied by the boom is minimized. Since the boom is collapsible to a small volume (of 1.5 m (H)×1.2 m (W)×5.0 m (L) in one embodiment) when stowed, the overall height of the inspection vehicle is substantially reduced when configured for transport. In one embodiment, the overall height of the inspection vehicle is about 2.6 m during transport when compared to a height of 4.0 m for conventional vehicles. This further allows transport of the vehicle by aircraft (such as a C-130 military transporter) for rapid deployment where appropriate.

Referring now to FIGS. 2a and 2b together, the vertical support sections 201a, 201b are manufactured using a strong material, which in one embodiment is steel. One of ordinary skill in the art would appreciate that other engineering materials such as carbon fiber composite, aluminum or metal-composite structures may also be used.

An advantage of the boom structure/design of the present invention is that the overall weight of the mobile inspection vehicle 200 is substantially reduced. For example, a full size 4.6 m (H)×3.5 m (W) scanning-tunnel vehicle has a total weight of less than 25,000 kg, preferably less than 20,000 kg, and more preferably less than 15,000 kg. Persons of ordinary skill in the art would appreciate that this weight of the mobile inspection vehicle of the present invention is substantially less when compared to a standard prior art truck that would typically weigh in excess of 25,000 kg. The lighter vehicle 200 of the present invention advantageously allows the vehicle/truck to operate with a single front axle and a single rear axle. Conventional designs require at least 2 and often 3 rear axles to meet road regulations in certain countries/regions due to comparatively high weights of prior art vehicles. This system also can achieve a penetration of steel of more than 90 mm, including 100 m, 120 mm, 150 mm, 180 mm and any increment therein.

Due to light weight, reduced number of axles and smaller overall size, the vehicle 200 of the present invention is much more capable of operating in rugged terrain than conventional prior art designs.

Figure 3A:
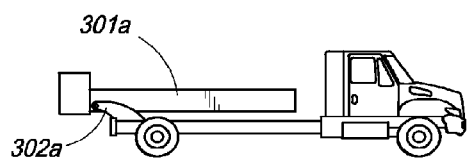
FIG. 3a depicts the functioning of a vertical support section of a boom according to one embodiment of the present invention.
Figure 3B:
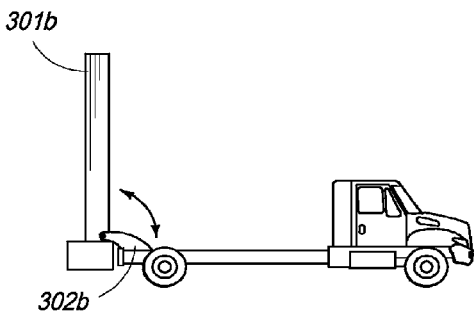
FIG. 3b depicts the functioning of a vertical support section of a boom according to another embodiment of the present invention.

The functioning of the vertical support is further detailed in FIGS. 3a and 3b. As shown in FIG. 3a, the vertical support 301a is in a near horizontal position when not deployed. In one embodiment, the vertical support 301a is at an angle in the range of 5 to 20 degrees to the horizontal, when in stowed away position. A fixed point 302a is provided, around which the vertical support is enabled to pivot around. Thus for deployment, the position of the vertical support 301a changes from near horizontal in FIG. 3a to vertical as depicted by 301b in FIG. 3b.

The rotating action of the vertical support over the fixed point 302a, 302b can be driven by a number of mechanisms including, but not restricted to, one or more hydraulic rams, one or more electric motors and associated gearboxes or a pulley drive system. It is preferable to be able to lock the vertical support in place once it has been rotated to the operating or stowed condition. This can be achieved by using, by way of example, conical pins (not shown) that pass through a support structure on the truck platform and into suitably located holes in the vertical support. One of ordinary skill in the art would appreciate that other locking mechanisms known in the art can also be used in place of or in addition to the example given.

Figure 4A:
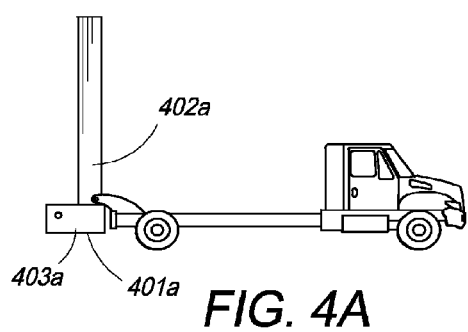
FIG. 4a depicts the mounting of a vertical support section of a boom on one embodiment of the mobile inspection vehicle in a deployed condition.

In one embodiment, the X-ray source of the scanning system is mounted rigidly to the base of the vertical support such that it swings close to the road surface once the vertical support is deployed. This is illustrated in FIG. 4a. Referring to FIG. 4a, the X-ray source 401a is mounted in an offset position on the vertical support 402a, such that the focal point 403a of the X-ray source is in line with the X-ray detectors (not shown) that, in one embodiment, are mounted into the horizontal and vertical boom structures (not shown in FIG. 4a). In this embodiment, the radiation source is positioned on the vertical support, which is a portion of the boom proximate to the truck, thereby offering a better alignment between the source and the detectors. In conventional inspection systems the radiation source is placed either on the truck itself, such as on the side or back of the truck, or on the distal end of the boom.

Figure 4B:
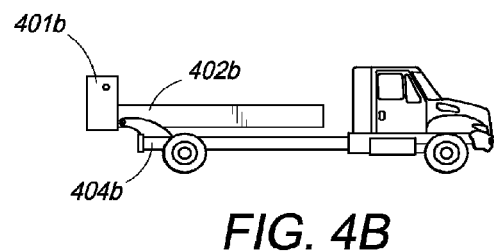
FIG. 4b depicts the mounting of a vertical support section of a boom on one embodiment of the mobile inspection vehicle in a stowed condition.

FIG. 4b shows the X-ray source 401b along with the vertical support 402b in the stowed position. It may be noted from FIG. 4b that substantially all of the weight of the vertical support 402b acts over, is in alignment with, or is otherwise positioned over the rear axle 404b of the truck. Therefore, the vertical support 402b is designed to minimize the overall weight of the mobile inspection vehicle in order to ensure that the rear axle loading is kept to a reasonable level.

Figure 28A:
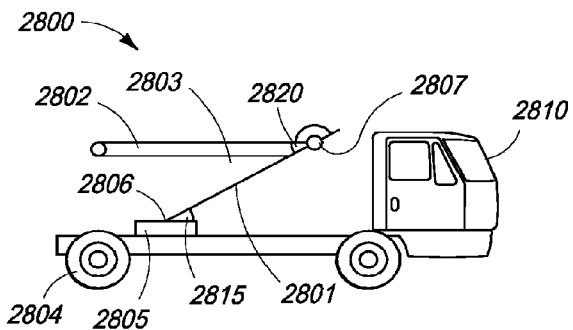
FIG. 28a shows an embodiment of boom structure/configuration to move pivot point of the boom forward of the rear wheels of the mobile inspection vehicle.

FIG. 28a shows a boom structure/configuration to move pivot point 2806 of the boom 2800 forward of the rear wheels 2804 of the mobile inspection vehicle 2810 in accordance with one embodiment of the present invention. In this embodiment, the boom 2800 comprises three components—vertical support 2801, horizontal boom 2802 and vertical boom 2803. The vertical support 2801 is mounted at its lower end to a rotating platform 2805 which is securely fixed onto the inspection vehicle chassis. An actuator is used to move the vertical support 2801 from a substantially horizontal (when stowed) to a vertical orientation about a hinge or pivot point 2806 which is attached to the rotating platform 2805. The horizontal boom 2802 is attached at one of its ends to the top of the vertical support 2801 using a pivot pin 2807. During deployment, as an actuator extends the vertical support 2801, a mechanical linkage maintains the same angle 2820 between the horizontal boom 2802 and vertical support 2801 as the angle 2815 between the vertical support 2801 and the rotating platform 2805. As a result, one actuator is used to extend two booms in one action or substantially concurrently.

Figure 28B:
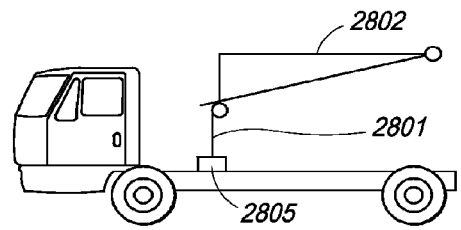
FIG. 28b shows vertical support of the boom of FIG. 28a extended in fully vertical orientation along with the horizontal boom being perpendicular to the vertical support.
Figure 28C:
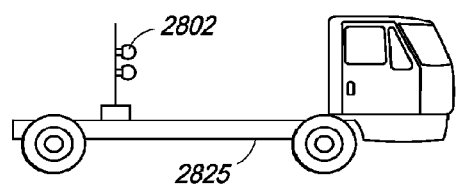
FIG. 28c shows the horizontal boom of the boom of FIG. 28a being rotated 90 degrees to be perpendicular to the long side of the mobile vehicle.
Figure 28D:
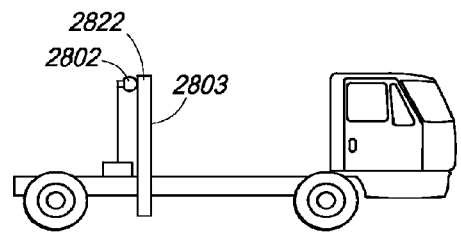
FIG. 28d shows the vertical boom of the boom of FIG. 28a being lowered down to complete full deployment.

FIG. 28b shows the vertical support 2801 extended in fully vertical orientation with reference to the rotating platform 2805 along with the horizontal boom 2802 also being perpendicular to the vertical support 2801. Once the vertical support 2801 and horizontal boom 2802 are deployed, as shown in FIG. 28b, another actuator is used to rotate the rotating platform 2805 through 90 degrees so that the horizontal boom 2802 is perpendicular to the long side 2825 of the vehicle and extending outwards as shown in FIG. 28c. Finally, as shown in FIG. 28d, a third actuator is used to lower the vertical boom 2803 from a hinge point 2822 at the distal end of the horizontal boom 2802.

Persons of ordinary skill in the art should note that the boom configuration of FIGS. 28a through 28d with the boom pivot point 2806 being advantageously forward of the rear wheels 2804 reduces rear axle load substantially, thereby making the inspection vehicle 2810 easier to drive and more compact while providing greater protection for the X-ray source (that is mounted at the lower end/base of the vertical support). Lower weight also contributes to faster deployment of the system. In one embodiment, the rear axle loading is below 9 tons for a full laden vehicle.

Figure 29A:
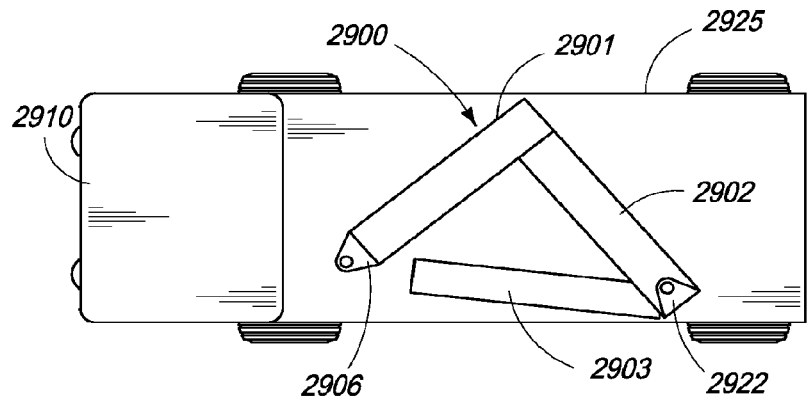
FIG. 29a shows an embodiment of structure/configuration of boom, when in stowed condition, in accordance with another aspect of the present invention.

FIG. 29a shows a top perspective of another embodiment of structure/configuration of boom 2900 when in stowed condition, in accordance with another aspect of the present invention. In this embodiment, the boom 2900 comprises two components—a first component comprising vertical support 2901 and horizontal boom 2902 and a second component comprising vertical boom 2903. The vertical support 2901 and horizontal boom 2902 are fixed at 90 degrees to each other to form one rigid assembly of the first component. The vertical boom 2903 is hinged from the distal end 2922 of the horizontal boom 2902.

Figure 29B:
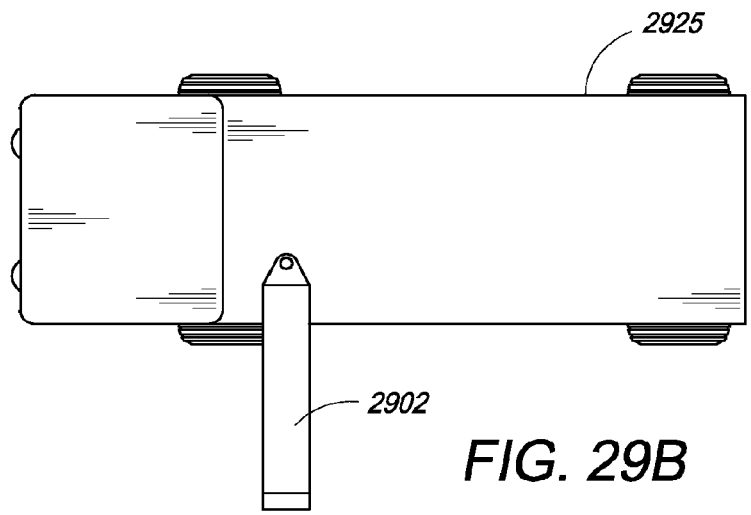
FIG. 29b shows vertical support of the boom of FIG. 29a in vertical position along with causing the horizontal boom to extend outwards in a direction perpendicular to the long edge of the vehicle.
Figure 29C:
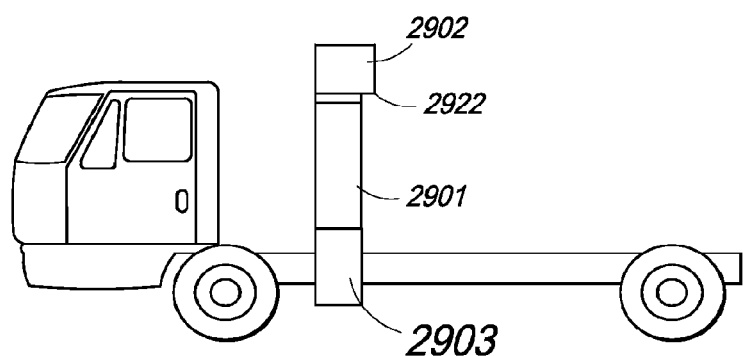
FIG. 29c shows the vertical boom of the boom of FIG. 29a being lowered down to complete full deployment.

The base of vertical support 2901 is hinged about a point 2906 which, in one embodiment, is at 45 degrees to the long edge 2925 of the side of the mobile vehicle 2910. Hinging the first component assembly (of the vertical support 2901 and horizontal boom 2902 at a fixed 90 degrees angle to each other) about the point 2906 causes the vertical support 2901 to become vertical (during deployment), from its starting horizontal aspect (when stowed), while simultaneously causing the horizontal boom 2902 to extend outwards in a direction perpendicular to the long edge 2925 of the vehicle, as shown in FIG. 29b. Again, as illustrated in FIG. 29c, once the vertical support 2901 and horizontal boom 2902 are in position, the vertical boom 2903 is lowered (using an actuator) about a hinge point at the distal end 2922 of the horizontal boom 2902 for complete deployment.

In one embodiment, it is preferred to have the vertical support 2901 comprising a first portion which is fixed rigidly to the chassis of the vehicle 2910 and a second part which is hinged from the top of the first part. In this case, the hinge will advantageously extend over an angle of greater than 90 degrees so that the intersection between the vertical support upper part and the horizontal boom 2902 lies nearer to the vehicle chassis.

Figure 30:
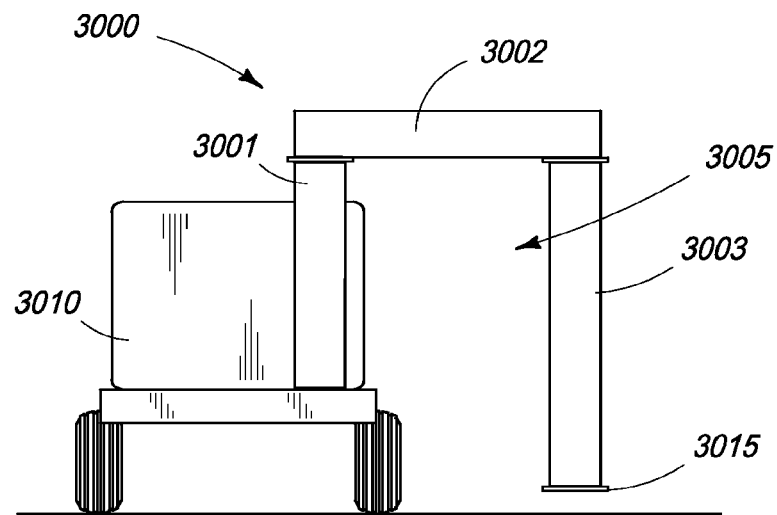
FIG. 30 shows an embodiment of the boom structure/configuration of the present invention where the boom is deployed using an onboard crane.

FIG. 30 shows yet another embodiment of structure/configuration of boom 3000 in accordance with an aspect of the present invention. In this embodiment, the boom 3000 comprises three components—vertical support 3001, horizontal boom 3002 and vertical boom 3003. The boom 3000 comprising these three components is stowed/loaded onto the back of the mobile vehicle 3010. Vehicle 3010 is provided with a manually operated crane (not shown), such as a Hiab lift, which is used to lift the boom sections into place to form a static archway 3005 that is used in drive-through portal mode. During deployment, in one embodiment, an operator lifts the vertical boom 3003 into position. Next, the operator lifts the vertical support 3001 into position. Finally, the operator lifts the horizontal boom 3002 into position such that it forms a 'bridge' between the vertical support 3001 and vertical boom 3003. At this point, the operator can stow the crane and the boom is ready for use.

In an alternate embodiment of the present invention, a positioning plate 3015 is first placed into position thereby setting an exact pre-determined location for the base of the vertical boom 3003 relative to the vehicle 3010. This positioning plate 3015 may be unfolded from the side of the vehicle or it may be placed into position using the vehicle mounted crane.

In a yet another alternative embodiment of the present invention, the vertical support 3001 and the vertical boom 3003 are each hinged from their respective ends of the horizontal boom 3002 to form an assembly. The vehicle mounted crane is used to lift the assembly of three components, from stowed condition, into approximate position for deployment. With the assembly suspended on the crane, the vertical support 3001 and vertical boom 3003 are lowered from a substantially horizontal position (that they were in when stowed) to a substantially vertical position using one or more electric or manually operated winches. The "inverted U" shaped boom 3000 is then lowered into its operating position and the crane removed to its storage position. The boom 3000 is then ready for use. To stow the boom, the crane is used to lift the assembly up, the vertical support 3001 and vertical boom 3003 are winched back to a substantially horizontal aspect and the thus assembly is stored back on the vehicle 3010.

Figure 31A:
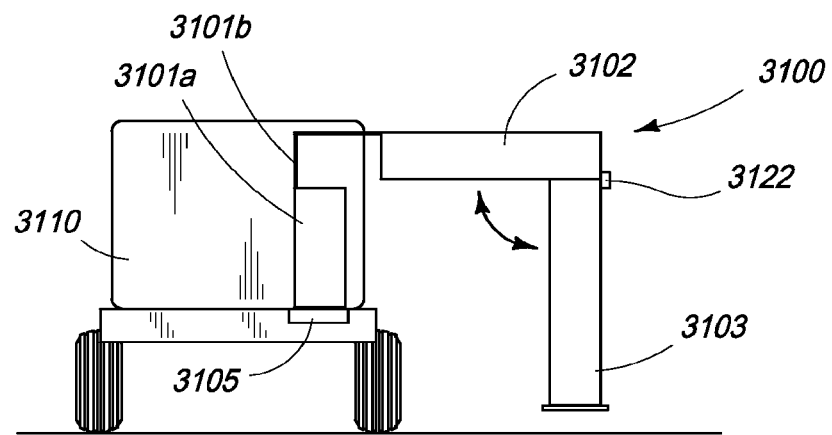
FIG. 31a shows an embodiment of the boom structure/configuration of the present invention comprising four components.

FIG. 31a shows still another embodiment of structure/configuration of boom 3100 in accordance with another aspect of the present invention. In this embodiment, the boom 3100 comprises four components—lower vertical support 3101a, upper vertical support 3101b, horizontal boom 3102 and vertical boom 3103. The lower vertical support 3101a is rigidly attached to a rotating platform 3105 while an actuator rotates the platform 3105 through 90 degrees in a plane perpendicular to the plane of the lower vertical support 3101a. The upper vertical support 3101b is attached to the lower vertical support 3101a using a hinge (not shown) which can rotate the two vertical support sections by 90 degrees with respect to each other. The upper vertical support 3101b is rigidly attached at 90 degrees to the horizontal boom 3102. The vertical boom 3103 is hinged at the end 3122 of the horizontal boom 3102 which is farthest from the upper vertical support 3101b. In stowed condition, the upper vertical support 3101b is folded substantially parallel to the lower vertical support 3101a.

Figure 31B:
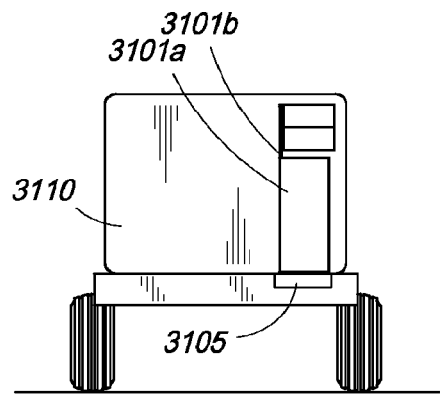
FIG. 31b shows the two vertical support sections of the boom of FIG. 31a unfolded into an end-to-end configuration.
Figure 31C:
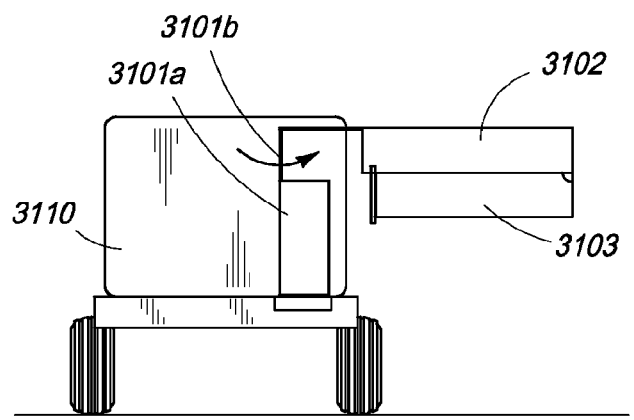
FIG. 31c shows the horizontal boom of the boom of FIG. 31a being extended perpendicular to the long edge of the vehicle through 90 degrees rotatory motion of the rotating platform.

To deploy the boom 3100, the two vertical support sections 3101a, 3101b are unfolded into an end-to-end configuration (that is, to make a single contiguous vertical support) as shown in FIG. 31b. The rotating platform 3105 then rotates the boom 3100 through 90 degrees such that the horizontal boom 3102 extends perpendicular to the long edge of the vehicle 3110, as illustrated in FIG. 31c. The vertical boom 3103 is then unfolded into the vertical direction to complete deployment of the boom, as has been depicted in FIG. 31a. Persons of ordinary skill in the art would appreciate that the boom stow sequence is exactly opposite to the above described deployment process.

In an alternate embodiment of the present invention, the upper and lower vertical support sections 3101b, 3101a respectively, are replaced by a single vertical support so that the boom is deployed by simply first rotating the boom and then unfolding the vertical boom 3103.

Figure 31D:
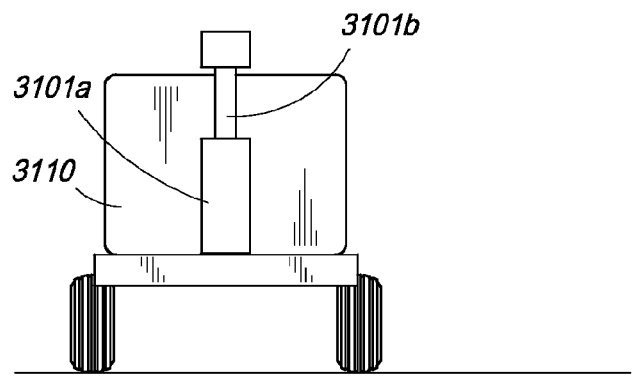
FIG. 31d shows an embodiment of the boom of FIG. 31a where the upper vertical support is telescopically retractable/extendable to/from the lower vertical support.

In another alternate embodiment of the present invention, upper vertical support 3101b is telescopically retractable/extendable to/from the lower vertical support 3101a as shown in FIG. 31d and is not hinged to the lower vertical support. In other words, for deployment the upper vertical support 3101b is simply extended vertically upwards; the platform 3105 rotated by 90 degrees and the vertical boom 3103 unfolded into vertical direction.

Figure 32A:
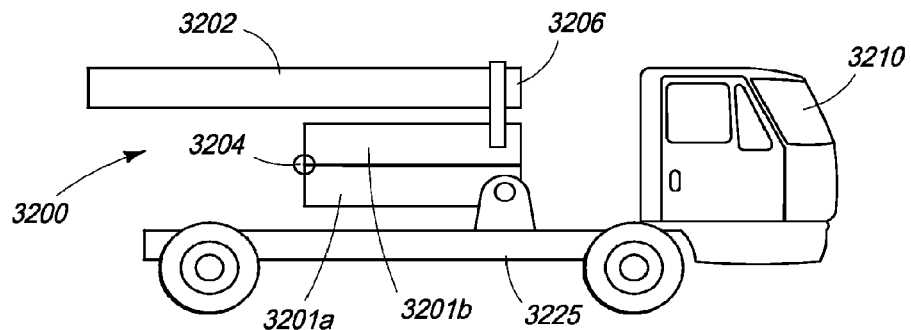
FIG. 32a shows an embodiment of the boom structure/configuration of the present invention comprising four components.

FIG. 32a shows yet another embodiment of structure/configuration of boom 3200, in stowed condition, in accordance with another aspect of the present invention. In this embodiment, the boom 3200 comprises four components—lower vertical support 3201a, upper vertical support 3201b, horizontal boom 3202 and vertical boom 3203 (visible in FIG. 32c). When stowed for transport, the lower and upper vertical support sections 3201a, 3201b respectively, are folded back on each other with rotating joints at each of their meeting ends 3204. The horizontal and vertical boom sections 3202, 3203 respectively, are each folded up to each other while the horizontal boom 3202 is attached to the upper vertical support 3201b using a pin bearing 3206.

Figure 32B:
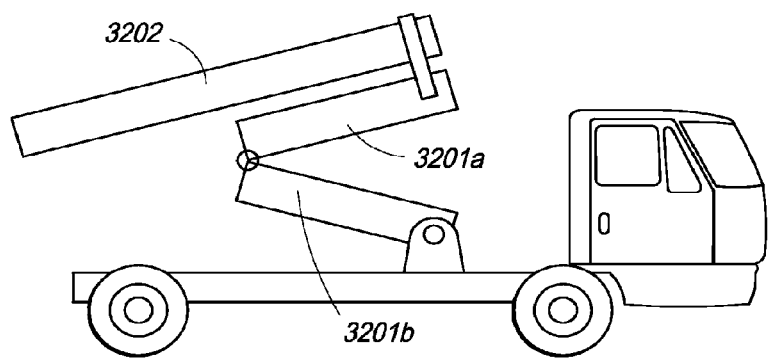
FIG. 32b shows the two vertical support sections of the boom of FIG. 32a extended from horizontal (stowed position) to vertical position.
Figure 32C:
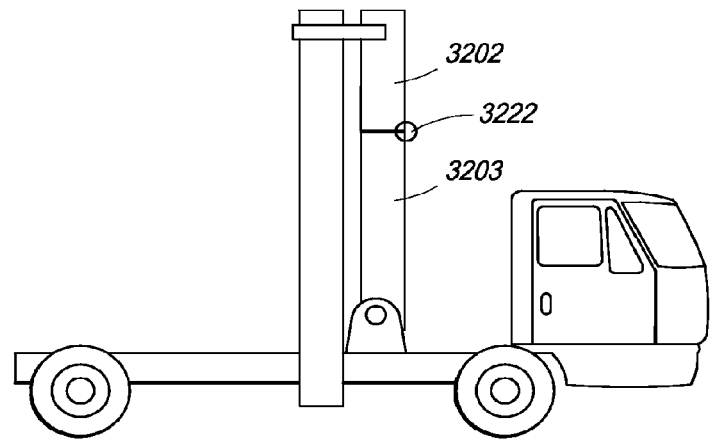
FIG. 32c shows the folded horizontal and vertical boom sections of the boom of FIG. 32a being moved from horizontal to vertical orientation.

During deployment, an actuator is used to extend the two vertical support sections 3201a, 3201b from the horizontal (stowed position) to vertical position, as shown in FIG. 32b. This causes the folded horizontal and vertical boom sections 3202, 3203 to move from the horizontal to the vertical orientation, as illustrated in FIG. 32c. An actuator then folds out the horizontal boom 3202 to horizontal aspect, taking the vertical boom 3203 with it. Finally, the vertical boom 3203 is lowered about its hinge point at the end 3222 of the horizontal boom 3202. Boom stow adopts the same sequence but in reverse order.

Referring back to FIG. 32a, in an alternate embodiment, the lower vertical support 3201a is mounted on to a rotating platform (not shown) which can be used to set angle of the resultant scanning tunnel (when the boom 3200 is fully deployed) such that it is in the range, typically, of 75 to 90 degrees with respect to the long edge 3225 of the vehicle 3210. Advantageously, X-ray source is fixed to the underside of the rotating platform so that it tracks the required beam angle.

Persons of ordinary skill in the art should note that the plurality of actuators, used for deployment or stow sequence of the boom structures of FIGS. 28 through 32 of the present invention, may be electric motor (with rotary gearbox or linear screw rod actuators), hydraulic cylinder and lever, electric winch and cable (with removable or fixed end points), manual winch and cable (with removable fixed end points) or any other actuators known to those skilled in the art. Where a rotating platform is used, boom deployment angles are adjustable in the range 75 degrees to 90 degrees with respect to the scanning direction. Also, scanning aperture of the boom structures/configurations of FIGS. 28 through 32 is typically 2000 mm (H)×2000 mm (W) minimum up to 5300 mm (H)×4000 mm (W) maximum. However, booms may alternatively be configured with a tunnel aperture outside these dimensions, such as 1000 mm (H), 3000 mm (H), 6000 mm (H), 7000 mm (H), 1000 mm (W), 3000 mm (W), 4500 mm (W), 5000 mm (W), 5500 mm (W), 6000 mm (W), 6500 mm (W), and any dimensions in between.

Again, X-ray sources may be selected from any of the following categories:
  X-ray tube and generator with 100 kVp to 500 kVp tube voltage and 0.1 mA to 20 mA tube current, including X-ray sources with 160 kV and a penetration of 30 mm of steel.
  0.8 MV to 2.5 MV linear accelerator source, including those sources with a low output dose rate, typically less than 0.1 Gy/min at 1 m.
  2.5 MV to 6 MV linear accelerator source with high output dose rate, typically in the range 0.1 Gy/min at 1 m to 10 Gy/min at 1 m.
  X-ray sources with penetration in excess of 120 mm of steel, including 180 mm of penetration and any increment therein.
  X-ray sources of 450 keV with a penetration of approximately 80 mm of steel.

In one embodiment, booms of the present invention are fitted with lead or steel beam stops to reduce primary beam intensity at the extent of the surrounding radiation exclusion zone. The beam stop is advantageously formed from lead with a thickness of 10 mm to 200 mm depending on the energy of the X-ray source (the higher the energy, the thicker the primary beam stop). The booms are fitted with X-ray detectors to measure the transmitted X-rays from the source through the object under inspection. Typically these detectors are formed from high density scintillation materials such as CdWO4, ZnWO4 or CsI with a thickness in the range 0.3 mm to 50 mm depending on the energy of the X-ray source and the type of transmission measurement being made.

Additionally or optionally, the booms of the present invention are fitted with position sensors to provide feedback to an automated boom deployment system. These sensors advantageously record when actuator motion is complete at both ends of travel. In one embodiment, redundant sensors are deployed for such measurements to mitigate against sensor failure.

In one embodiment for example, it is possible to complete boom deployment in less than 2 minutes. Still faster times may be achieved when suitable strengthening components are fitted to the various booms to mitigate actuator load. Further, boom stowage can also be completed in a similar duration of time.

The horizontal and vertical booms in the scanning system of the present invention are designed to contain as little material as possible. This allows for minimizing the weight, and hence reduces the tipping moment on the truck chassis. Several materials can be selected for manufacturing the booms, including steel, aluminum and composite materials. One of ordinary skill in the art would appreciate that other suitable light weight materials may also be used for this purpose. In one embodiment, the boom design utilizes novel lattice structures to ensure low mass in the boom. FIGS. 5a through 5d illustrate some of the exemplary low mass lattice structures which act to reduce the weight of the booms. The booms are further designed to include a light-tight, but compact housing for the X-ray detector assemblies.

Figure 5A:
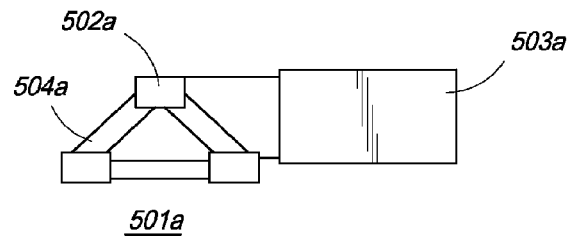
FIG. 5a illustrates a first configuration of an exemplary low mass lattice structure which acts to reduce the weight of the boom, as used in one embodiment of the present invention.

Referring to FIG. 5a, a section of the boom 501a is shown in cross-section. This boom structure utilizes square profile box section components 502a, or nodes, where three such box section components 502a are physically connected by a beam section 504a. The sensor box 503a is mounted to the side of the boom structure using metal support brackets (not shown) which attach to the triangular boom section 501a.

Figure 5B:
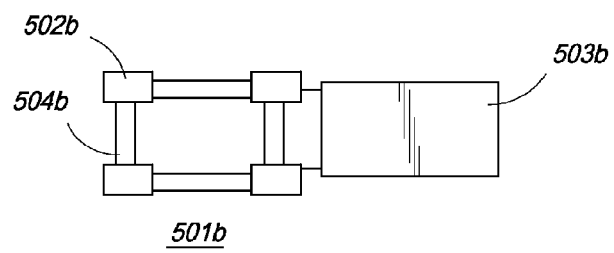
FIG. 5b illustrates a second configuration of an exemplary low mass lattice structure which acts to reduce the weight of the boom, as used in one embodiment of the present invention.

FIG. 5b shows an alternate design in cross-section, wherein the boom has a square cross section 501b with the sensor components 503b mounted to the side and is made from four square profile box section components 502b where the components 502b are physically connected by a beam section 504b. One of ordinary skill in the art would appreciate that it would also be possible to mount the sensor box 503b within the square section 501b. This, however, would result in a weakening of the structure since the sensor box would need to form a "U" shape to allow unimpeded access of X-rays to the detectors.

Figure 5C:
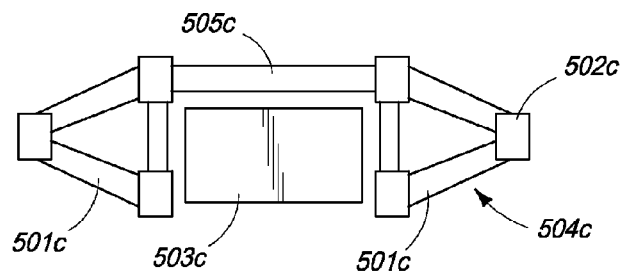
FIG. 5c illustrates a third configuration of an exemplary low mass lattice structure which acts to reduce the weight of the boom, as used in one embodiment of the present invention.

FIG. 5c shows a further design in which the detector box 503c is protected within a boom section comprised of two triangular support frames 501c of the boom. Each of the triangular support frames 501c comprises three profile box section components 502c where the components 502c are physically connected by a beam section 504c. The two triangular sections are then further physically connected by beam section 505c.

Figure 5D:
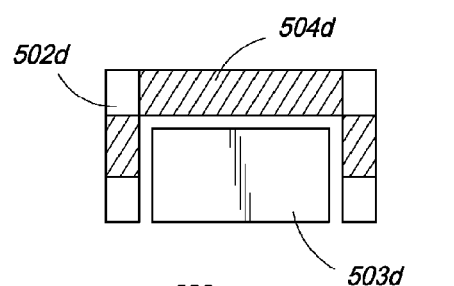
FIG. 5d illustrates a fourth configuration of an exemplary low mass lattice structure which acts to reduce the weight of the boom, as used in one embodiment of the present invention.

FIG. 5d shows another design of the boom in which "bulkheads" 504d are mounted along the length of the boom which itself is formed from box section components 502d. The sensor box 503d in this case is encased within the boom section.

One of ordinary skill in the art would appreciate that many other structures may also be used for the boom design to fulfill the objective of low mass, including, for example, round section tubing and cast composite structures. The use of open frame lattice structures and detector enclosures such as illustrated above not only makes the boom lightweight, but also makes it less wind resistant due to flow through, while still maintaining its rigidity.

Figure 6:
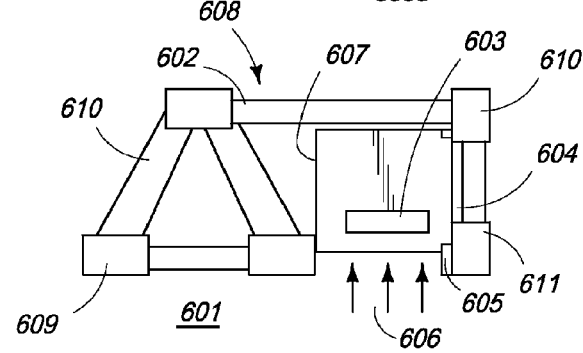
FIG. 6 shows an exemplary design for a combined boom and detector box.

The detector box used with the boom is required to be light, tight and impervious to moisture. By way of good design, in one embodiment, the detector box is combined with the boom structure to provide additional strength while also providing good access to the detector electronics. FIG. 6 shows an exemplary design for a combined boom and detector box. Referring to FIG. 6, the boom cross section 601 is extended to include a box section 602 for the X-ray detectors by connecting a beam section 608 from one of its three profile box section components 609 where the components 609 are physically connected by beam sections 610. Beam section 608 physically connects to a box component 610, which then connects to a second box component 611. The detector electronics 603 are provided with removable access covers 604 on one side and a removable front cover 605 which is substantially transparent to the incoming X-rays 606. Further, a thin light-tight sheet covering 607 is provided to protect the rear side of the assembly and the side opposite to the access cover.

The lattice structures for boom and detector box illustrated in FIGS. 5 and 6 can be fabricated using any suitable technique known to persons of ordinary skill in the art. As an example, it would be advantageous to fabricate the structure shown in FIG. 6 using a welded fabrication of 50 mm×50 mm steel box section components with 2.5 mm wall thickness to which 1 mm thick steel sheet is welded to form the detector enclosure, the detector cover and the access covers. Preferably, the detector box is lined with a thermal insulation material to minimize thermal shock to the detectors due to change in ambient temperature and also to help in reducing condensation that may occur in particularly cold climates.

In one embodiment of the system of present invention, only one common engineering material is used for boom fabrication. This not only proves cost-effective, but also ensures that uneven deformation in the boom does not occur under change in ambient temperature as may be the case when multiple materials are used in a boom design.

As mentioned earlier, one objective of the present invention is to ensure a compact method of stowing the boom when not deployed. In order to fold the horizontal boom out from the vertical support for deployment, a number of mechanisms may be used. FIG. 7 presents an exemplary design for folding and unfolding boom sections, as used in one embodiment of the present invention. Referring to FIG. 7, a single hydraulic arm 701 is used to force the separation of the horizontal boom 702 from the vertical support 703. The separation is facilitated by means of an intermediate rigid coupling 704 which rotates about a point 705 on the vertical support.

In one embodiment, the unfolding action illustrated in FIG. 7 is complimented by a locking pin arrangement so that after deployment, hydraulic power can be lost without the boom folding back up. An exemplary locking mechanism is shown in FIGS. 8a and 8b. Referring to FIGS. 8a and 8b, the horizontal boom 801a is extended so that it folds back above the vertical support 802a. A dome shaped fixture 803a, 803b attached rigidly to the top of the vertical support 802a engages with locking plates 804a, 804b in the horizontal boom. The locking plates 804a, 804b are spring loaded such that they are pushed back when the boom is being folded by the dome shaped structure 803a, 803b on the vertical support 802a. Once the boom 801a is deployed fully, the locking plates 804a, 804b snap back to their resting position under the dome and the boom is locked in position. When the boom 801a is to be stowed, the locking plates 804a, 804b can be withdrawn using any suitable means, such as an electrical solenoid, electric motor, hydraulic actuator or any other device known to persons of ordinary skill in the art. A person of ordinary skill in the art would also appreciate that many other locking mechanisms may also be devised that provide a good balance between efficiency, cost and safety.

Figure 9:
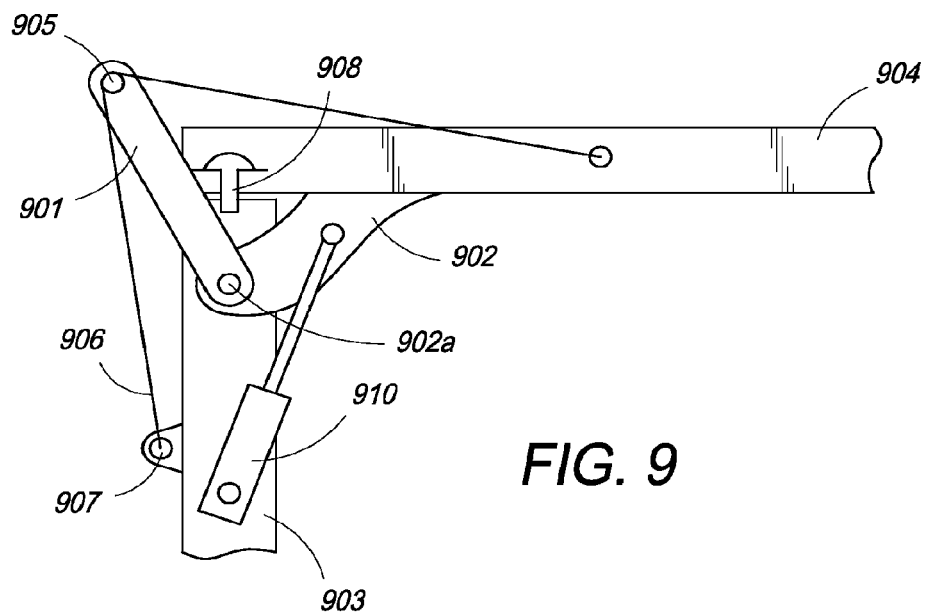
FIG. 9 shows an additional boom support structure which can optionally be used to help the boom deployment.

FIG. 9 shows another boom deployment structure. In this case, a first end of a support bar 901 mounts to a bearing post 902, which connects vertical support 903 to horizontal boom 904 in an angular configuration. Preferably the support bar 901 connects to the bearing post 902 at the bearing post pivot point 902a. A second end of the support bar 901 has integrated therein a pulley 905, distal to the bearing 902. A cable 906 connects to the horizontal boom 904 and passes over the pulley 905 and returns back to a winch 907 which is mounted securely onto the vertical support 903. The winch 907 is operated during boom deployment and it acts to pull the horizontal boom 904 away from the vertical support 903. This mechanism eliminates the need for a hydraulic actuator, although a hydraulic support 910 may be employed for safety or backup. FIG. 9 also shows a horizontal boom lock 908, which may be used to sense when the boom deployment action has completed, so that the winch 907 can be stopped. Preferably a sensor is deployed in conjunction with the horizontal boom lock 908 to sense a locking action and transmit the sensed locking action to a controller, which then communicates a stop signal to the winch based upon the locked state.

Figure 10:
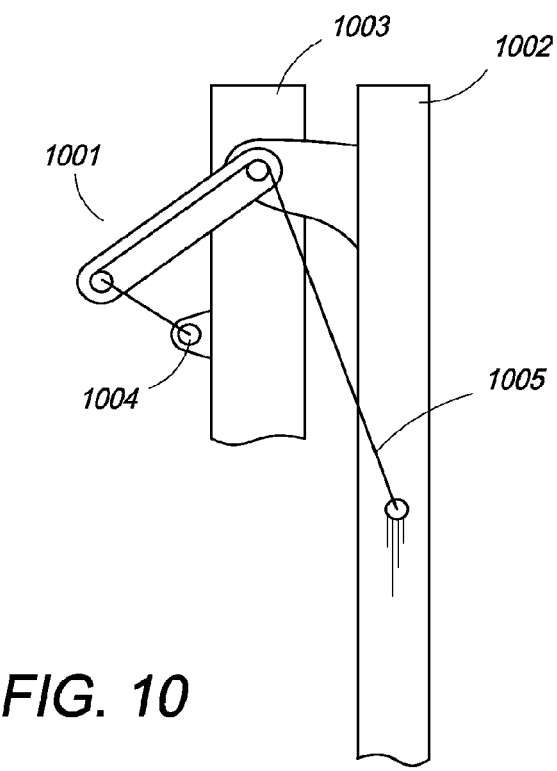
FIG. 10 shows another boom support structure.

A further enhancement of this invention is shown in FIG. 10. Referring to FIG. 10, the support bar 1001 is designed such that it can be rotated out of the way once the horizontal boom 1002 has been stowed with the vertical support 1003 using the mechanism of the winch 1004 and cable 1005. As the support bar 1001 is moved away, it serves to minimize the space taken by the stowed boom.

Figure 11A:
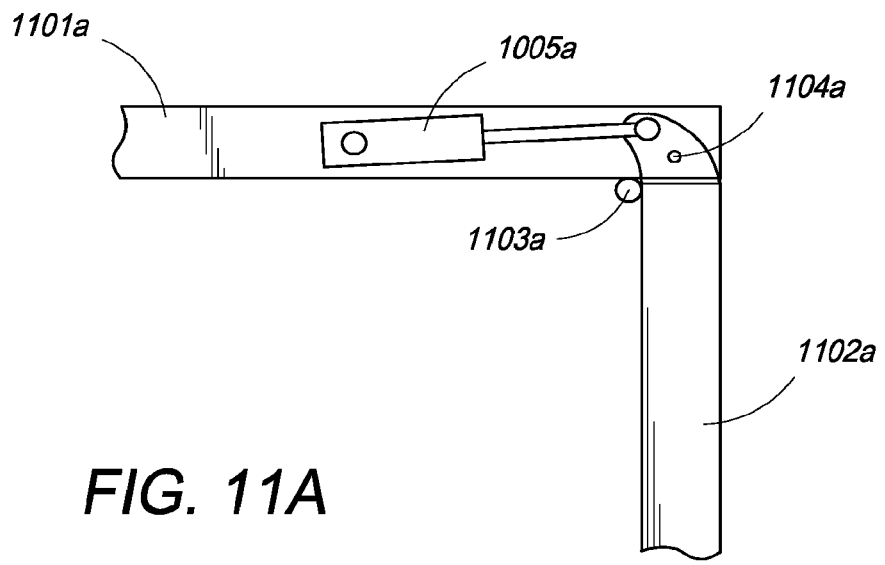
FIG. 11a illustrates a first space saving folding arrangement between a horizontal boom and vertical boom, according to one embodiment of the present invention.
Figure 11B:
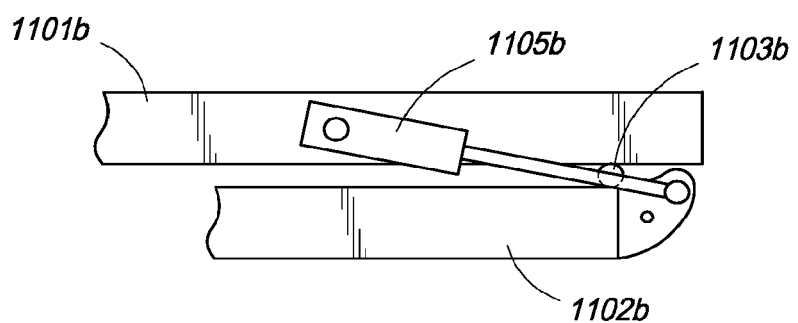
FIG. 11b illustrates a second space saving folding arrangement between the horizontal boom and vertical boom, according to one embodiment of the present invention.

Besides an efficient and compact folding arrangement between the vertical support and the horizontal section of the boom, the design of the present invention also incorporates a space saving folding arrangement between the horizontal boom section and vertical boom section, which is illustrated in FIGS. 11a and 11b. Referring to FIG. 11a, which shows the boom in a deployed state, at the junction of the horizontal section 1101a and vertical section 1102a, a single folding hinge arrangement 1103a is used. A locking pin 1104a is also provided which engages when the booms 1101a and 1102a are deployed fully, and acts to minimize mechanical wobble between the two booms. A single hydraulic ram 1105a is used to force the separation of the horizontal section 1101a from the vertical section 1102a when unfolding is required.

The booms in folded or stowed state are illustrated in FIG. 11b, wherein the hydraulic ram 1105b works in conjunction with the hinge arrangement 1103b to fold the vertical boom 1102b parallel to the horizontal boom 1101b.

One of ordinary skill in the art would appreciate that the aforementioned folding arrangement between the horizontal boom and vertical boom is provided as an example only, and several other designs can be implemented successfully.

Persons of ordinary skill in the art should also note that the boom structures of the present invention allow requisite accuracy of alignment so that X-ray energy levels of less than 2 MeV can be used while also being adequate enough to penetrate 150 mm of steel, in accordance with one embodiment. Further, as a result of the use of lower X-ray energy levels, the embodiments of the present invention use smaller Linacs when compared to prior art systems, thereby saving on overall weight. As a further result of the cumulative weight savings, the present invention allows for an X-ray mobile inspection system with penetration greater than 120 mm of steel, while weighing less than 15,000 kg.

Figure 12A:
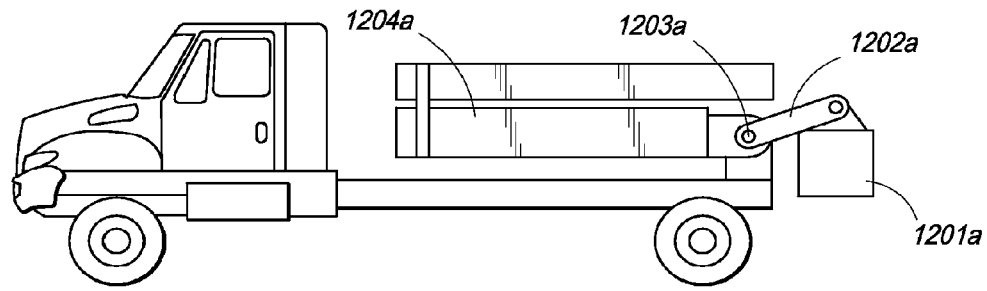
FIG. 12a illustrates an exemplary boom configuration which limits the rotation of the X-ray source.
Figure 12B:
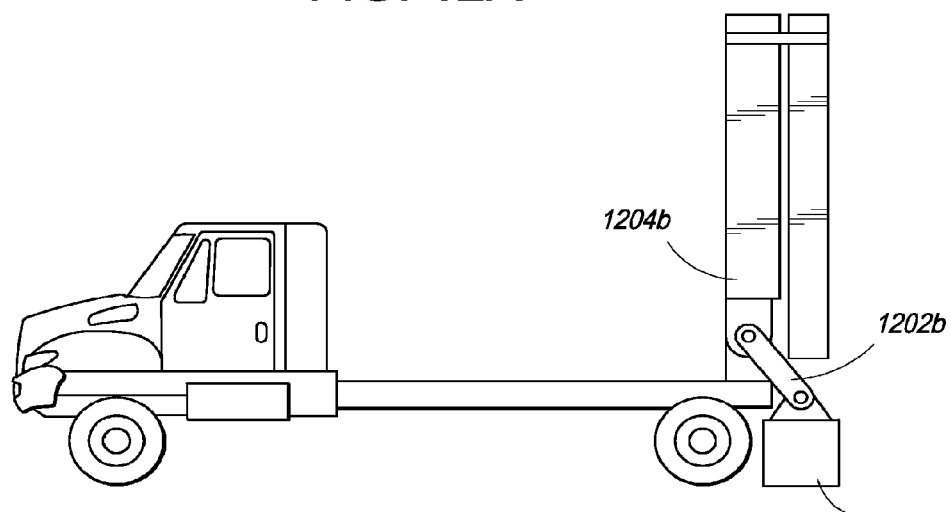
FIG. 12b illustrates another exemplary boom configuration which limits the rotation of the X-ray source.

In a further aspect of this invention, the system is advantageously configured to avoid rotation of the X-ray source. This boom configuration which limits the rotation of the X-ray source is illustrated in FIGS. 12a and 12b. Referring to FIG. 12a, an alternate X-ray source mounting is shown, with the boom structure in a stowed position. Here, the X-ray source 1201a is suspended from a bracket 1202a which is able to rotate about a point 1203a fixed to the boom structure 1204a. FIG. 12b illustrates the configuration with the boom structure in a partially deployed position. Referring to FIG. 12b, as the vertical support structure 1204b is raised for boom deployment, the X-ray support bracket 1202b lowers the X-ray source 1201b towards its final operating point based upon a signal from a controller. This arrangement avoids the rotation of the X-ray source itself for boom deployment.

Figure 13A:
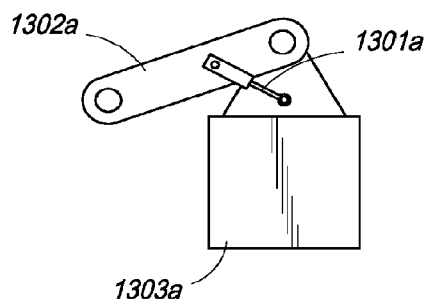
FIG. 13a illustrates an exemplary mechanism for minimizing the swinging movement of the X-ray source during boom deployment.
Figure 13B:
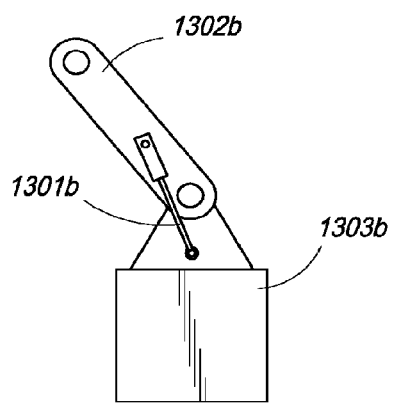
FIG. 13b illustrates another exemplary mechanism for minimizing the swinging movement of the X-ray source during boom deployment.

In one embodiment, the swinging movement of the X-ray source during boom deployment is also minimized by connecting a hydraulic damping system between the X-ray source bracket and the X-ray source itself. This arrangement is shown in FIGS. 13a and 13b. Referring to FIG. 13a, which shows the system in an undeployed position, a hydraulic cylinder 1301a links the X-ray support bracket 1302a and the X-ray source 1303a. Hydraulic cylinder 1301a comprises fluid flow valves that are opened during boom deploy and stow, such that the cylinder can change length under the effect of gravitational pull on the X-ray source. Referring to FIG. 13b, once the boom is deployed, the fluid valves of hydraulic cylinder 1301b are closed, thereby locking the X-ray source 1303b in position along with the X-ray support bracket 1302b. One of ordinary skill in the art would appreciate that final adjustment of source position can be made by extending or retracting the hydraulic cylinder as necessary, depending on the gradient of the ground on which the main X-ray system is operating.

Figure 14A:
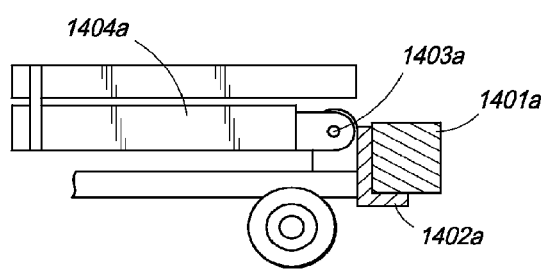
FIG. 14a illustrates a configuration for mounting the X-ray source.
Figure 14B:
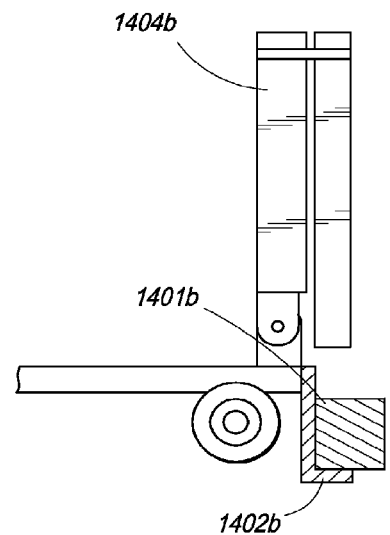
FIG. 14b illustrates an alternative configuration for mounting the X-ray source.

An alternative configuration for mounting the X-ray source is illustrated in FIGS. 14a and 14b. Referring to FIG. 14a, the X-ray source 1401a is mounted on a platform 1402a, which is fixed rigidly to the motionless part of the rotation joint 1403a at the base of the vertical support 1404a. The platform 1402a is capable of being raised and lowered for stowing and deployment respectively. Accordingly, the platform is physically slidable relative to the truck. Referring to FIG. 14b, when the vertical support structure 1404b is raised for boom deployment, the platform 1402b is concurrently lowered, thereby placing the X-ray source 1401b in its final operating position. The platform 1402b can be moved up, down, right, or left to position the source correctly for scanning. It should be appreciated that this motion can be effectuated through a motor, engine, or hydraulic system, as is well known to persons of ordinary skill in the art.

Figure 15A:
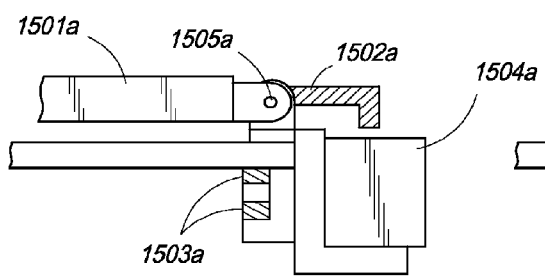
FIG. 15a illustrates an exemplary locking mechanism for the boom and the X-ray source.
Figure 15B:
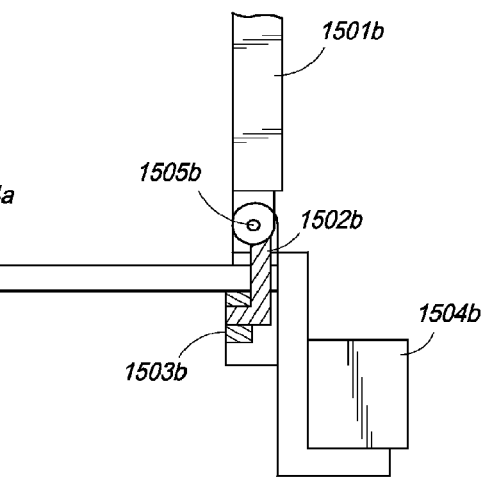
FIG. 15b illustrates another exemplary locking mechanism for the boom and the X-ray source.

In one embodiment, the platform on which the X-ray source is mounted is actuated using one or more hydraulic rams. Further, the hydraulic ram is operated in conjunction with a geared chain drive so that the change in length of the hydraulic ram can indirectly effect a change in position of the X-ray source relative to the boom rotation point. A mechanical arrangement is also provided to lock the relative positions of the boom and the X-ray source. One such exemplary locking mechanism is shown in FIGS. 15a and 15b. Referring to FIG. 15a, which shows the system in stowed position, the vertical support section 1501a is provided with a first locking element 1502a, designed to mate with a corresponding, or mating, locking element or fixture 1503a in the platform assembly 1504a. Thus, when the boom is deployed as shown in FIG. 15b, the first locking element 1502b and the corresponding, or mating, locking element 1503b are connected in a such a manner that the relative positions of the boom 1501b and X-ray source 1504b are fixed exactly. The locking element 1502a, 1502b rotates about a pivot point 1505a, 1505b to thereby move approximately 90 degrees and be received by the corresponding, or mating, element 1503a, 1503b and thereby transition from an unlocked state to a locked state. One of ordinary skill in the art would recognise that many alternative locking mechanisms are possible in addition or in place of the exemplary locking mechanism described above.

The X-ray system used with the mobile inspection system of the present invention is designed to allow use with a wide range of X-ray sources. The source of radiation may include conventional sources such as a radio-isotopic source or an X-ray tube, as well as Linear Accelerators (LINAC) or any other source known in the art capable of producing beam flux and energy sufficiently high to direct a beam to traverse the space through an object under inspection to detectors at the other side, such as a betatron. The choice of source type and its intensity and energy depends upon the sensitivity of the detectors, the radiographic density of the cargo in the space between the source and detectors, radiation safety considerations, and operational requirements, such as the inspection speed.

For example, the system of the present invention could employ source-based systems, cobalt-60 or cesium-137 and further employ the required photomultiplier tubes (PMT) as detectors. If a linear accelerator (LINAC) is optionally employed, then photodiodes and crystals are used in the detector. One of ordinary skill in the art would appreciate how to select a radiation source type, depending upon his or her inspection requirements. In one embodiment, the system is operated with a standard X-ray tube, which typically has energy in the range of 120 kVp to 450 kVp, for applications such as screening cars and small vehicles with or without passengers within the vehicle. In another embodiment, a low energy linear accelerator source, having a typical energy in the range of 0.8 MV to 2 MV, is used for the purposes of screening full size cargo in manifest verification. In yet another embodiment, a higher energy X-ray source, typically with an energy range of 2.5 MV to 6 MV, is used for scanning of full-sized containers. In this case, the image penetration capability of the X-ray source is suitable for detection of a range of illicit materials and devices including narcotics, explosives, currency, alcohol, weapons and improvised explosive devices. Those skilled in the art would further appreciate that the inspection system of the present invention may also be configured with a gamma-ray source such as Co-60 or Cs-137, to replace the X-ray source.

Regardless of whether the radiation source is an X-ray generator or a LINAC, it is mounted on the same single boom as the detector arrays, so that the need for sophisticated alignment systems each time the system is deployed is eliminated. Thus, the radiation source and detectors are substantially permanently aligned on the same single boom. The feature also allows for scanning at various degrees of offset, again without the need to realign the LINAC or X-ray generator and detectors.

The X-ray system of the present invention is further designed to operate with a very compact radiation footprint. As known in the art, X-ray scanning operates on the principle that, as X-rays pass through objects, the radiation gets attenuated, absorbed, and/or deflected owing to a number of different physical phenomena that are indicative of the nature of the material being scanned. In particular, scattering occurs when the original X-ray hits an object and is then deflected from its original path through an angle. These scatter radiations are non-directional and proportional to the total energy delivered in beam path. A narrowly collimated beam will keep the overall radiation dose minimal and therefore also reduce the amount of scatter radiation in the area surrounding the scanner, thereby reducing the "exclusion zone". The exclusion zone is an area around the scanner in which general public are not authorized to enter due to the possibility of their getting exposed to doses of radiations scattered during the scanning process. The exclusion area is dependent upon the magnitude of current setting the intensity of the radiation source. The availability of a large enough area for the "exclusion zone" around the scanner system is one of the factors that influence the decision of positioning the mobile inspection system.

Thus, in order to achieve a compact radiation footprint, and hence a smaller exclusion zone, it is necessary to collimate the radiation beam down to a narrow fan beam of X-rays. This is illustrated in FIGS. 16a and 16b. In the embodiment shown in FIG. 16a, the X-ray beam 1601a is wide compared to the X-ray detector 1602a, so that the detector 1602a is always illuminated regardless of movement of the boom. Alternatively, as shown in FIG. 16b, the detector 1602b is wider than the illuminating beam 1601b, thereby ensuring continuous illumination at the detector regardless of movement of the boom. In either case, it is advantageous to ensure that the boom design minimizes motion between the source and sensors. The folding boom structure of the present invention can achieve this objective by mounting the X-ray source and X-ray sensors to the same folding array structure so that relative motion between the three boom assemblies (horizontal boom, vertical boom and vertical support) is minimized. In this way the X-ray source (or accelerator) and the X-ray detector are better aligned in the scanning system of the present invention, than in boom designs used with other scanning systems.

Furthermore, the X-ray system of the present invention is designed to operate in rugged conditions such as those employed in military applications. As described earlier, the compact nature of the boom design, in particular its fold-flat capability, makes the mobile inspection system of the present invention uniquely suited to military applications where it may be frequently required to transport the X-ray system in its stowed condition in aircraft or helicopters. Such frequent transportation is not feasible with other known boom configurations, where the height of the boom in its stowed condition is greater than that allowed for military transport. Further, the compact configuration lends a low center of gravity for better stability of the inspection system during road transport, as there is often a need for driving the inspection system in hilly areas, border crossings, and steep mountainous areas.

The X-ray system used with mobile inspection system of the present invention is further intended to be deployed in a variety of configurations. Some of these exemplary configurations are illustrated in FIGS. 17a through 17c. Referring to FIG. 17a, the X-ray boom structure 1701a is demounted from a vehicle or truck (not shown) and used as a standalone trailer (shown as 1702a) mounted device. The trailer mounted system of FIG. 17a, which has wheels, can be used as a scanning system by attaching the trailer to a winch system which can drag the trailer backwards and forwards along a track. Alternatively, the trailer can be fitted with a speed sensing system so that the trailer can be used to scan drive through traffic.

In an alternate configuration, illustrated in FIG. 17b, the scanning system 1701b is used as a standalone device that can be dropped off the back of a truck bed 1702b. The standalone system of FIG. 17b will normally be used in a drive through mode although it may also be used with a winch to scan unoccupied vehicles (vehicle moves through static gantry).

In a third configuration, as shown in FIG. 17c, the scanning system 1701c can be fully integrated with a truck 1702c for mobile applications. This integrated system is typically used as a drive past scanner in which the X-ray system is driven past a stationary object at controlled speed. However, in this case, it is also possible to operate the system in a drive through mode. Here the boom base is attached directly to the truck bed or to a trailer which is then integrated with the truck bed. A suitable sensor configuration for control of the X-ray system when operating in drive through mode is shown in FIG. 14. The sensor system is used to execute two functionalities—traffic control and X-ray control.

Figure 24:
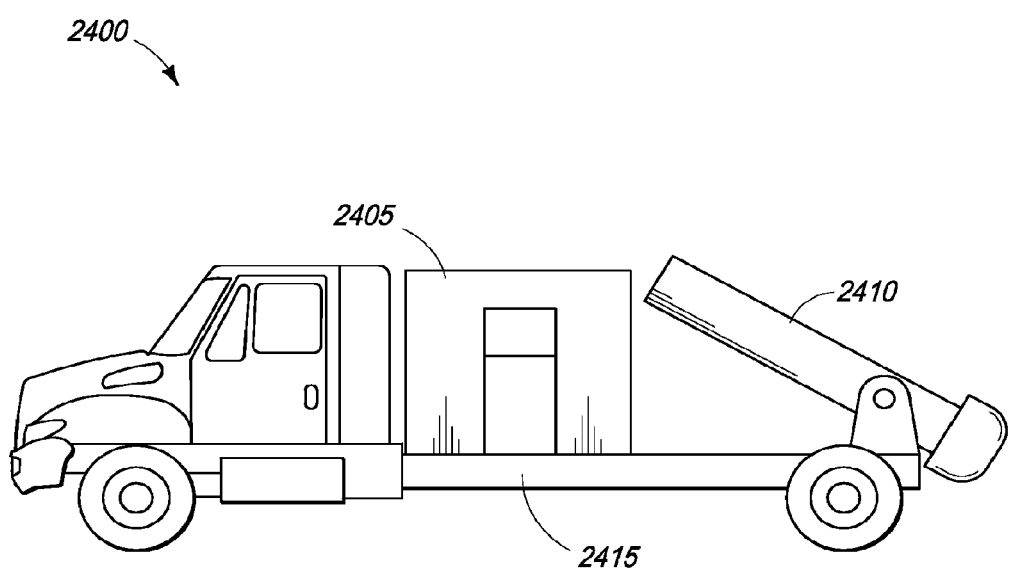
FIG. 24 shows a side elevation view of the mobile inspection vehicle of the present invention comprising an inspection pod in accordance with one embodiment.

In one embodiment, the mobile inspection vehicle 2400 of the present invention comprises an inspection pod 2405, placed on vehicle bed 2415 along with stowed boom 2410, as shown in the side elevation view of the vehicle 2400 of FIG. 24. The inspection pod 2405 accommodates at least one inspector who can view scanned X-ray images on a monitor while being seated facing either the front or back of the vehicle. In one embodiment, the inspection pod 2405 is sized to allow two image inspectors to be seated back to back.

Figure 25A:
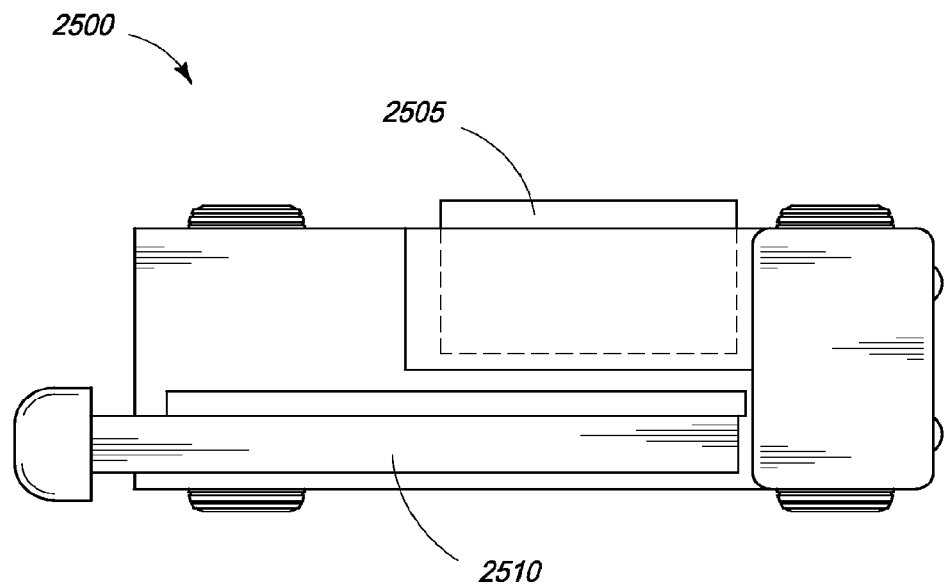
FIG. 25a shows top view of the mobile inspection vehicle of the present invention comprising an inspection pod in retractable state for travel.
Figure 25B:
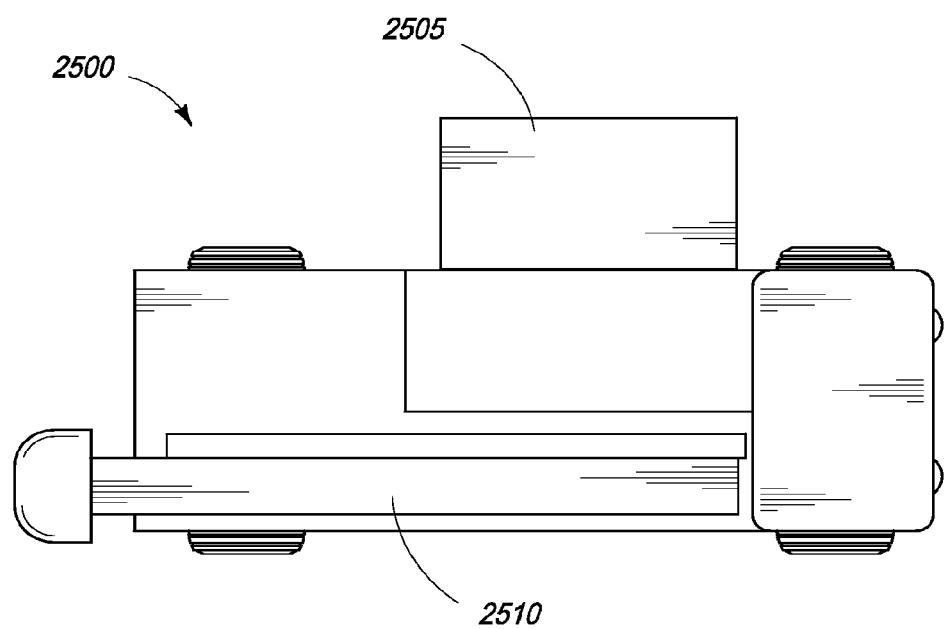
FIG. 25b shows top view of the mobile inspection vehicle of the present invention comprising the inspection pod in extendable state during deployment/operation.

Referring now to FIGS. 25a, b, the inspection pod 2505, in one embodiment, is configured to be in retractable state and accommodated completely on-board the vehicle 2500 ready for travel as shown in the top view of FIG. 25a and in extendable state when deployed for scanning as shown in the top view of FIG. 25b. Persons of ordinary skill in the art should note that the inspection pod 2505 is sized to be comfortably accommodated on-board the vehicle 2500 such that when in retractable state it is placed next to the stowed boom 2510. During operation, in one embodiment, when the boom 2510 is being deployed the inspection pod 2505 is also simultaneously extended thereby keeping the overall time for system deployment low.

In one embodiment, keeping in mind the overall compactness of the vehicle 2400 and the stowed boom 2410, the inspection pod 2405 is sized at a footprint of about 2 m (L)×1 m (W)×2.5 m (H) when retracted (during travel) and of about 2 m (L)×2 m (W)×2.5 m (H) when in extended state during deployment/inspection. The sliding pod 2405 of the present invention enables a smaller footprint during travel while allowing for up to two inspectors to be seated, within, in extended state during inspection or deployment.

Figure 26A:
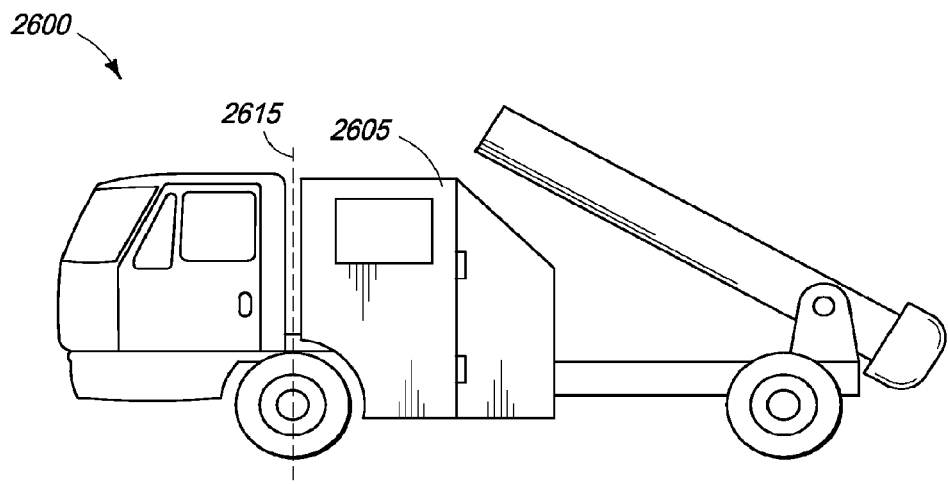
FIG. 26a shows a side elevation view of the mobile inspection vehicle of the present invention comprising inspection pod accessible to an inspector that can be seated above front wheel level.
Figure 26B:
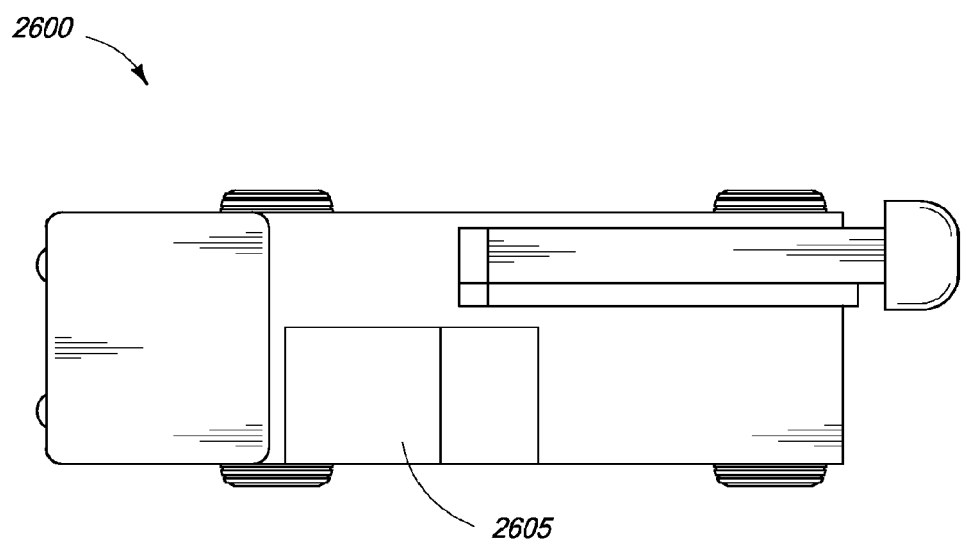
FIG. 26b shows top view of the mobile inspection vehicle of the present invention comprising inspection pod accessible to an inspector that can be seated above front wheel level.

In an alternate embodiment of FIGS. 26a and 26b, the inspection pod 2605 is located on the mobile inspection vehicle 2600 such that the inspector is seated just above the wheel level 2615 with access to the pod 2605 through a hinged door (not shown). This configuration results in a lower overall inspection pod height. However, in this embodiment, the inspector is always seated within the pod. In the embodiment of FIGS. 25a and 25b, the placement of the pod on the vehicle along with its height allows the inspector(s) to also stand up in the pod when needed.

Figure 27:
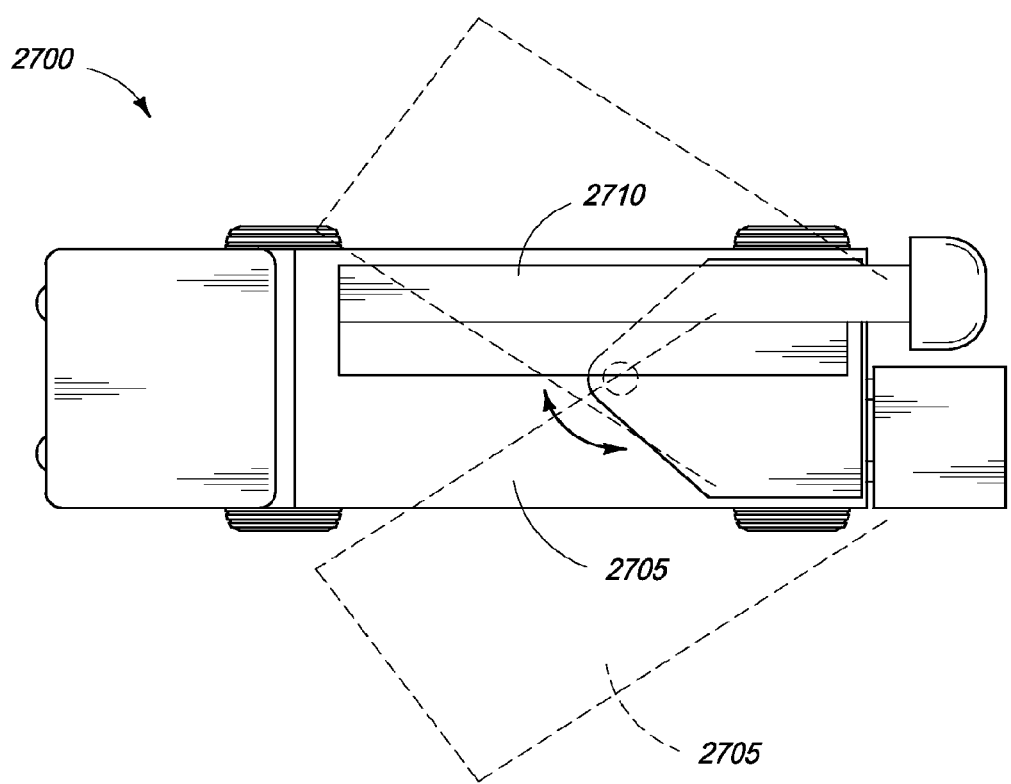
FIG. 27 shows top view of the mobile inspection vehicle of the present invention that has a rotatable bed.

FIG. 27 shows a yet another embodiment of the mobile inspection vehicle 2700 of the present invention where the vehicle bed 2705, that supports the stowed boom 2710 along with the attached X-ray source 2715 can be swiveled or rotated by a plurality of angles in the horizontal plane of the bed. In one embodiment, the bed 2705 is capable of being swiveled to angles that allow deployment of the boom 2710 at customized angles ranging from, say, 70 to 90 degrees with respect to the direction of scan. As would be evident to persons of ordinary skill in the art, the rotation of the bed 2705 is typically controlled, in one embodiment, using electric motor or hydraulic actuator with accompanying sensors to confirm rotation angle.

Referring now to FIG. 18, the sensor system comprises one or more microwave based radar speed camera 1801 mounted on the horizontal boom 1802 of the scanning system 1800. The use of more than one redundant sensor is advantageous in this safety critical aspect of the design. The radar sensors 1801 are used to sense the speed of a vehicle passing though the X-ray aperture of the scanning system 1800 for inspection. For maintaining accuracy of measurement, the measured speed value is updated at regular intervals. In one embodiment, the speed value is measured and updated approximately ten times a second so as to reflect the speed of the vehicle passing though the scanning system as precisely as possible. Also, for obtaining optimum scan results with a scanning system, there is generally a preferred speed at which a vehicle being scanned should pass through, however the system of present invention allows for a range of vehicle speeds. For example in one embodiment, an optimum speed for a vehicle to pass through is 8 km/h, but acceptable vehicle speeds can range between 5 km/h and 10 km/h, with optimum results.

The traffic control or the speed control mechanism of the present invention is designed to assist the driver of the vehicle being inspected to drive through the system at an acceptable speed. In one embodiment, a green traffic signal 1803 is presented to the driver when the speed of the vehicle is within acceptable range. If the driver slows down to below the lower acceptable speed limit, an amber colored up arrow 1804 is illuminated in addition to or in place of the green traffic signal 1803. Alternatively, if the driver passes through at a speed above acceptable upper speed limit, an amber-colored down arrow 1805 is illuminated in addition to or in place or the green traffic signal 1803.

The X-Ray control mechanism of the present invention allows for automatic determination of the frequency and energy of the X-ray beam used for illumination of the vehicle or cargo being inspected. For this purpose, the mechanism takes into account variables such as the start of the driver's cab, the end of the driver's cab, the starting point of the cargo to be inspected and the end point of cargo to be inspected. The X-ray control mechanism comprises two redundant methods for imaging the target vehicle and determining the aforementioned variables. The first method involves use of a scanning laser sensor 1806, which forms a two dimensional image of the height above the road surface of the vehicle being inspected. The second method of imaging the vehicle involves use of a machine vision camera 1807, which is located on the vertical support 1808. The machine vision camera 1807 detects vision targets 1809 that are placed on the vertical boom 1810 on the opposite side. The vision targets 1809 are located such that they correspond to different parts of a cargo vehicle. Therefore, the simultaneous analysis of a number of different targets can be used to identify different parts of the vehicle driving through the inspection aperture. By combining signals from the machine vision camera 1807 and the scanning laser sensor 1806, a robust control mechanism for switching on the X-ray beam according to the requirements can be implemented.

Figure 19:
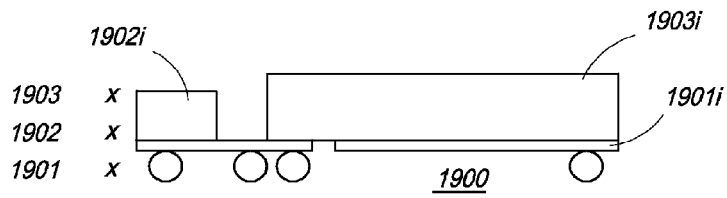
FIG. 19 shows an exemplary location of three vision targets, with respect to a vehicle being inspected.

FIG. 19 shows an exemplary location of three vision targets (described with reference to 1809 in FIG. 18); with respect to a vehicle 1900 being inspected. In this example, the vehicle 1900 is a truck. The first target 1901 is located in line with the base of the vehicle flatbed 1901i. The second target 1902 is located in line with the cab of the vehicle 1902i, and the third target 1903 is located in line with the highest part of the cargo 1903i. A vision target can comprise any material capable of being readily identified by a camera and differentially seen by a camera relative to the vehicle surface.

Figure 20:
FIG. 20 shows the output from a scanning laser sensor as a function of time.

FIG. 20 shows the output from the scanning laser sensor (described with reference to 1806 in FIG. 18) as a function of time. Four discrete transitions are indicated, representing various parts of the vehicle being scanned. The first transition A 2001 occurs when the start of the vehicle cab is detected. The second transition B 2002 occurs when the end of the vehicle cab is detected. The third transition C 2003 occurs at the start of cargo, and the fourth transition D 2004 occurs at the end of cargo.

FIG. 20 further depicts (by means of marking with a tick) which of the three vision targets detailed in FIG. 19 will be visible at each transition 2001, 2002, 2003, 2004, as detected by the laser height scanner. Thus, as shown in FIG. 20, target3 2005, which is placed in line with highest part of the cargo, is visible during transitions A 2001, B2002 and D 2004, which indicate start of the vehicle cab, end of the vehicle cab, and end of the cargo respectively. Similarly, target2 2006, which is located in line with the cab of the vehicle, is visible during transitions B2002 and D 2004, which indicate the end of the vehicle cab and end of the cargo, respectively. Target1 2007, which is located in line with the base of the vehicle flatbed, is not visible in any of the transitions.

Figure 21:
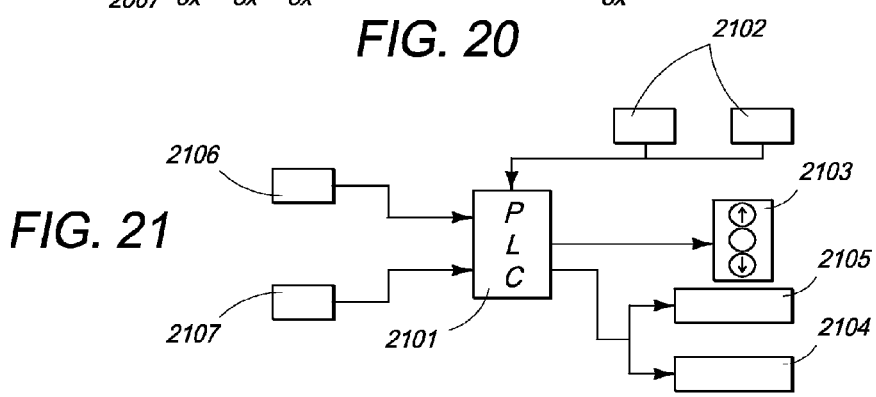
FIG. 21 illustrates an embodiment where a process logic controller (PLC) is used to control the traffic control and X-ray control mechanism in the scanning system of the present invention.

In one embodiment, a safety rated process logic controller (PLC) is used to control the traffic control and X-ray control mechanism. This system is illustrated in FIG. 21. A process logic controller (PLC) 2101 takes inputs regarding the vehicle speed from the radar sensors 2102, compares the values provided by the various radar sensors, and outputs traffic control signals 2103 depending on the drive-through vehicle speed. In one embodiment, the current vehicle speed is displayed on an electronic sign whose value is updated frequently, such as once per second.

The radar sensor data is also processed to provide a speed output to the X-ray system, comprising the X-ray source 2104 and the X-ray sensors 2105. The PLC 2101 changes the frequency at which each line of X-ray data is collected, in proportion to the speed of the vehicle passing through the inspection area. For example, if the system normally operates at 300 Hz at 8 km/h, the frequency is increased to 375 Hz at a drive through speed of 10 km/h and reduced to 188 Hz at a drive through speed of 5 km/h. This kind of frequency modulation in accordance with the vehicle speed results in delivery of a constant dose of radiation per unit length of the vehicle. This in turn ensures good image quality and consistent scattered radiation dose to the driver and surrounding system operators.

The PLC 2101 also receives inputs from the scanning laser sensor 2106 and the machine vision camera 2107, and controls the generation of X-Ray beam in accordance with the dimensions of the vehicle and cargo being inspected. One of ordinary skill in the art would appreciate that additional sensors can be employed in the scanning system and interfaced with the PLC 2101 to provide greater levels of safety and accuracy as required. For example, in one embodiment, a set of tire sensors can be deployed with the scanning system, which would allow the system to produce X-rays only when the driver's cab is safely past the primary X-ray beam.

It is imperative that the X-ray sensor system is designed appropriate to the application. In general, it is good practice to design a high spatial resolution sensor system, and to blur the image at the time of data display in order to create a low dose imaging system with good contrast resolution and penetration capability. This blurring can be achieved by mixing different proportions of the sharp original image with a blurred version until a good diagnostic image is obtained for the feature of interest.

At any point in time when the radiation source is on, the detectors are snapshots of the radiation beam attenuation in the object under inspection (OUI) for a particular "slice" of the OUI. Each slice is a beam density measurement, where the density depends upon beam attenuation through the OUI. The radiation detectors convert the lateral radiation profile of the OUI into electrical signals that are processed in an image processing system, housed in the inspection trailer, while the OUI is being conducted past the source and the radiation detector.

The X-ray image processing and control system, in an exemplary embodiment, comprises computer and storage systems which record the detector snapshots and software to merge them together to form an X-ray image of the vehicle which may further be plotted on a screen or on other media. The X-ray image is viewed or automatically analyzed by OUI acquisition system such as a CRT or monitor that displays the X-ray image of the vehicle to an operator/analyst. Alternatively, the OUI acquisition systems may be a database of X-ray images of desired targets, such as automobiles, bricks or other shapes that can be compared with features in the image. As a result of this imaging, only articles that were not contained in the reference image of the container or vehicle are selectively displayed to an operator/analyst. This makes it easier to locate articles that do not correspond to a reference condition of the container or vehicle, and then to conduct a physical inspection of those articles. Also, for high-resolution applications, the electronics used to read out the detector signals may typically feature auto-zeroed, double-correlated sampling to achieve ultra-stable zero drift and low-offset-noise data acquisition. Automatic gain ranging may be used to accommodate the wide attenuation ranges that can be encountered with large containers and vehicles.

The present invention generates a graphical representation, i.e., an image, of the densities of the contents of the vehicle under inspection. This allows for easy visual interpretation of the results of the scanning of the OUI. Advantageously, the preferred software system also causes the display of a reference image simultaneously with the image generated in response to the vehicle under inspection, so that an operator of the present embodiment can easily make a visual comparison between what an object of the type being inspected should "look like", and what the OUI actually "looks like". Such "side-by-side" inspection further simplifies the detection of contraband using the present embodiment.

Figure 22:
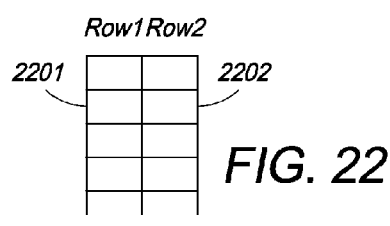
FIG. 22 illustrates an exemplary detector configuration according to one embodiment of the present invention.

The present invention employs a detector configuration which provides a good compromise between image spatial resolution, contrast and penetration performance and cost. This detector configuration is schematically illustrated in FIG. 22, and is particularly useful when using a low dose, low energy X-ray source such as a linear accelerator in the energy range 0.8 MV to 2 MV. Referring to FIG. 22, a two row sensor arrangement is shown, in which both rows of sensors—2201 and 2202, are irradiated by the X-ray beam. The pulsed X-ray beam (not shown) from the linear accelerator is timed such that each X-ray pulse occurs when the object relative to the X-ray beam moves exactly by one detector spacing. This means that the two adjacent detector samples can be summed with the advantage of doubling the detected signal, while at the same time reducing the X-ray photon noise by a square root of two. This arrangement enhances the signal to noise ratio in the scanning system of the present invention by around 40% as compared to systems using a single row of detectors.

It may be noted that when using the aforementioned detector arrangement, the design of the present invention also ensures that the boom itself is very stable, so that the X-ray beam can be collimated tightly in order to minimize the operational radiation footprint of the X-ray scanning system.

Such a detector configuration has the benefit of allowing a double drive-through rate where the vehicle moves exactly two detector widths through the X-ray beam between X-ray pulses. This can increase the nominal drive through speed from for example, 8 km/h to 16 km/h, albeit with a reduction in image penetration performance but with no reduction in spatial resolution.

Such a detector configuration has a further benefit of allowing dual-energy imaging when provided with an X-ray linear accelerator that is capable of interleaved energy operation. That is, the system can work with small and large accelerators at low and high energy. For example, two energies—of the order of 3 MV and 6 MV may be used in adjacent pulses. In one embodiment, each pulse is delivered after the object to be inspected has passed exactly one detector width through the X-ray inspection aperture. The vehicle will therefore have completely passed the detector after exactly two X-ray pulses, one at low energy and one at high energy. Although the penetration performance is somewhat compromised since only one measurement is made at each beam energy and not two, however, this information is very useful in providing materials discrimination performance.

In one embodiment, where the present invention employs dual source-based systems, it further employs the required photomultiplier tubes as detectors. In one embodiment, $^{60}$Co is used as a first gamma ray source and has a high specific activity of the order of 11.1 TBq (300 Ci) and a linear dimension of the active area of 6 mm. In one embodiment, the second gamma ray source is a 1.0, 1.6 or 2.0 Curie shuttered mono-energetic source of $^{137}$Cs gamma rays, having 662 keV energy.

Figure 23:
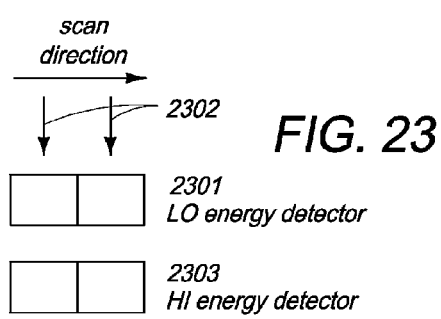
FIG. 23 illustrates another exemplary configuration wherein the detectors are stacked, according to one embodiment of the present invention.

In a further embodiment of the present invention, stacked detectors can be used to provide further spectral deconvolution of the X-ray beam. This is illustrated in FIG. 23. Referring to FIG. 23, one set of low energy detectors 2301 are located in the path of the X-ray beam 2302, and a second set of detectors 2303 are shadowed from the X-ray source by the first set of detectors 2301. In this case, the second set of detectors 2303 can see only the high energy part of the X-ray beam. This information can be effectively used to provide materials discrimination capability in the scanning system of the present invention. In another embodiment, both stacked detectors and an interleaved X-ray source may be used to provide an enhanced level of materials discrimination performance.

In one embodiment, additional collimation is advantageously provided adjacent to the detector array. This may be achieved for example, by placing thin sheets of tungsten or other suitably attenuating material parallel to the direction of the X-ray beam but orthogonal to the detector array. Such collimation acts to reduce the effect scatter created in the detector housing assembly as well as scatter generated within the object under inspection.

One of ordinary skill in the art would appreciate that spatial resolution that can be achieved in the X-ray image depends on the detector configuration chosen and on the focal spot size of the X-ray source. In one embodiment, the detectors are configured with an element size in the range of 1 mm to 10 mm and the X-ray source has a focal spot dimension in the range of 0.5 mm to 3 mm. This results in a spatial resolution generally between 1 lp/cm and 5 lp/cm.

Further, the penetration performance depends on the energy of the X-ray source. For the system of present invention, the penetration performance is typically in the range of 20-100 mm for X-ray sources below 450 kVp, between 100 mm and 200 mm for sources in the range of 450 kVp to 2 MV and between 200 mm and 400 mm for sources in the range of 2 MV to 6 MV.

In a further aspect of this invention, the X-ray imaging system is integrated with a passive gamma detection system. In this case, one or more large area detectors are located adjacent to the X-ray detector arrays in the horizontal and vertical booms and along the full length of the vertical support. This arrangement provides a large surface area for gamma-ray detection. In one embodiment, the large area gamma ray detectors are advantageously assembled from organic scintillation materials such as an organic plastic scintillator or using in-organic scintillator materials such as NiI(Tl) of CsI(Tl). The gamma-ray detectors are advantageously also configured to allow them to be switched off while the X-ray source is switched on and then re-enabled once the X-ray beam is switched back off again. This is particularly important when using a pulsed linear accelerator source for X-ray imaging where the gamma-ray detectors can be rendered inactive during the X-ray pulse and re-activated immediately following the pulse.

In another configuration, the secondary detectors can provide a simultaneous backscatter imaging capability. In this case, X-rays from the main imaging beam may backscatter into a series of detectors which are mounted upon the vertical support. In one embodiment, the detectors may be provided with additional collimation in order to restrict the direction from which backscattered radiation is received. The backscatter image, being correlated in spatial position with the X-ray transmission image, can provide additional information about the presence, or otherwise, of low atomic number materials that are located at, or near to, the surface of the object under inspection adjacent to the X-ray source.

The novel design and the aforementioned features of the present invention enable a cost-effective, safe and completely self-contained scanning system that can be used for non-intrusive inspection of containers, trucks and passenger vehicles. The road mobile configuration and low weight design of the present scanning system allows for transport on difficult terrain, such as in border areas, apart from local roads and highways. Further, since the system takes a very short time (around 15 minutes) to be fully deployed, and there is less operational space required for deployment, it facilitates operation at multiple locations and is efficient at performing high throughput inspections. The system can scan cargo in mobile and stationary mode and the minimal operating area makes it well suited for limited space applications. Some of the other features and benefits of the mobile inspection system of the present invention are:

The boom design allows for more precise linear accelerator to detector alignment. The folded array detector box configuration shortens the distance between X-ray source and the detector, which increases penetration and provides no corner cutoff with less image distortion.

The unique scanning boom assembly can be deployed at either a ninety or a eighty degree offset to the vehicle inspected. This allows maximum flexibility in the setup of operational area while providing excellent hidden compartment and false wall detection capabilities.

One person may deploy the boom with a single button; thus the system is safe, reliable and simple. Stowing the boom is done in the same manner.

The scanning system includes a plurality of CCTV cameras, which provide a view of the operating zone and help maintain safety.

Two modes of operation are supported—Mobile and Portal, which allow for inspection of stationary as well as moving cargos, respectively.

A training mode is provided, which offers images from a training library for simulated scans during inspector training.

The modular design of the scanning boom assembly and imaging system allows it to be easily adapted to truck chassis from several different manufacturers. This allows local trucks to be utilized in various countries and simplifies vehicle maintenance.

The above examples are merely illustrative of the many applications of the system of present invention. Although only a few embodiments of the present invention have been described herein, it should be understood that the present invention might be embodied in many other specific forms without departing from the spirit or scope of the invention. For example, other configurations of cargo, tires, tankers, doors, airplane, packages, boxes, suitcases, cargo containers, automobile semi-trailers, tanker trucks, railroad cars, and other similar objects under inspection can also be considered. Therefore, the present examples and embodiments are to be considered as illustrative and not restrictive, and the invention is not to be limited to the details given herein, but may be modified within the scope of the appended claims.

We claim:

1. An inspection system comprising:
   a vehicle having a bed defining a horizontal surface;
   a boom attached to said vehicle wherein said boom comprises a lower vertical support section, an upper vertical support section, a horizontal boom section and a second vertical boom section, wherein said lower and upper vertical support sections are movably attached to each other and wherein the lower vertical support section is mounted on to a platform such that an angle of a resultant scanning tunnel when the boom is fully deployed is in an angular range of 75 to 90 degrees with respect to said horizontal surface of the vehicle;
   a radiological source rotatably attached to the lower vertical support section to produce a radiation beam for scanning at said angular range; and
   an array of detectors attached to at least one of said sections of the boom, wherein the array of detectors remain stationary and aligned with the radiological source during the scanning operation.

2. The system of claim 1, wherein said platform is configured to be rotatable.

3. The system of claim 1, wherein said lower and upper vertical support sections are configured to be folded against each other when the boom is stowed.

4. The system of claim 1, wherein said second vertical boom section is hinged to said horizontal boom section.

5. The system of claim 1, wherein said horizontal and second vertical boom sections are configured to be folded against each other when the boom is stowed.

6. The system of claim 1, wherein the horizontal boom section is attached to the upper vertical support section using a pin bearing.

7. The system of claim 1, wherein a boom deployment angle is adjustable in the angular range of 75 degrees to 90 degrees with respect to a scanning direction.

8. The system of claim 1, wherein said radiological source is an X-ray source is at least one of an X-ray generator with 100 kVp to 500 kVp tube voltage and 0.1 mA to 20 mA tube current, a 0.8 MV to 2.5 MV linear accelerator source with a dose output rate of less than 0.1 Gy/min at 1 m, and a 2.5 MV to 6 MV linear accelerator source with an output dose rate in a range 0.1 Gy/min at 1 m to 10 Gy/min at 1 m.

9. The system of claim 1, wherein said boom comprises X-ray detectors to measure a plurality of transmitted X-rays from the radiological source through an object under inspection.

10. The system of claim 1, wherein said boom comprises position sensors to provide feedback to an automated boom deployment system.

11. An inspection system comprising:
    a vehicle having a first axle proximate to a front of said vehicle and at least one rear axle proximate to a back of said vehicle;
    a boom attached to said vehicle wherein said boom has a weight and comprises a lower vertical support section, an upper vertical support section, a horizontal boom section and a second vertical boom section, wherein said lower and upper vertical support sections are pivotably attached to each other and wherein the lower vertical support section is mounted on to a platform such that an angle of a resultant scanning tunnel when the boom is fully deployed is in an angular range of 75 to 90 degrees with respect to said vehicle;
    a radiological source rotatably attached to the lower vertical support section to produce a radiation beam for scanning at said angle; and
    an array of detectors attached to at least one of said sections of the boom, wherein the array of detectors remain stationary and aligned with the radiological source during said scanning operation.

12. The system of claim 11, wherein said platform is adapted to rotate.

13. The system of claim 11, wherein said lower and upper vertical support sections are folded against each other when the boom is stowed.

14. The system of claim 11, wherein said second vertical boom section is hinged to said horizontal boom section.

15. The system of claim 11, wherein said horizontal and second vertical boom sections are folded against each other when the boom is stowed.

16. The system of claim 11, wherein the horizontal boom section is attached to the upper vertical support section using a pin bearing.

17. The system of claim 11, wherein a plurality of angles defining a boom deployment are adjustable in the angular range of 75 degrees to 90 degrees with respect to a scanning direction.

18. The system of claim 11, wherein said system is configured to achieve radiological penetration of at least 30 mm of steel.

19. The system of claim 11 wherein a first area is bounded by the rear axle extending to the front of said vehicle and a second area is bounded by the rear axle extending to the back of said vehicle and wherein a weight of the boom is positioned to be over said first area and not said second area and wherein said system weighs 25,000 kg or less.

20. The system of claim 11, wherein said boom has a lattice structure comprising a plurality of beam sections connected by a plurality of nodes, wherein said structure defines an internal lattice area.

* * * * *